(12) United States Patent
Escames Rosa et al.

(10) Patent No.: US 8,962,673 B2
(45) Date of Patent: Feb. 24, 2015

(54) USE OF MELATONIN FOR TREATING AND/OR PREVENTING MUCOSITIS

(71) Applicant: Universidad de Granada, Granada (ES)

(72) Inventors: Germaine Escames Rosa, Granada (ES); Dario Acuna Castroviejo, Granada (ES)

(73) Assignee: Universidad de Granada, Granada (ES)

( * ) Notice: Subject to any disclaimer, the term of this patent is extended or adjusted under 35 U.S.C. 154(b) by 0 days.

(21) Appl. No.: 14/352,617

(22) PCT Filed: Oct. 18, 2012

(86) PCT No.: PCT/ES2012/070728
§ 371 (c)(1),
(2) Date: Apr. 17, 2014

(87) PCT Pub. No.: WO2013/057354
PCT Pub. Date: Apr. 25, 2013

(65) Prior Publication Data
US 2014/0243384 A1 Aug. 28, 2014

(30) Foreign Application Priority Data
Oct. 19, 2011 (ES) .................................. 201101158

(51) Int. Cl.
| | | |
|---|---|---|
| A61K 31/404 | (2006.01) | |
| A61K 31/4045 | (2006.01) | |
| A61K 47/10 | (2006.01) | |
| A61K 9/00 | (2006.01) | |
| A61K 9/06 | (2006.01) | |

(52) U.S. Cl.
CPC ............. *A61K 31/4045* (2013.01); *A61K 47/10* (2013.01); *A61K 9/006* (2013.01); *A61K 9/06* (2013.01)
USPC ........................................................ 514/415

(58) Field of Classification Search
USPC ........................................................ 514/415
See application file for complete search history.

(56) References Cited

U.S. PATENT DOCUMENTS

| | | |
|---|---|---|
| 2011/0112654 A1 | 5/2011 | Faldt |
| 2011/0237563 A1 | 9/2011 | Costantini |

FOREIGN PATENT DOCUMENTS

| | | |
|---|---|---|
| WO | 03024391 | 5/2003 |
| WO | 03088986 | 10/2003 |
| WO | 2008018106 | 2/2008 |
| WO | 2010062153 | 6/2010 |
| WO | 2010118461 | 10/2010 |

OTHER PUBLICATIONS

"Extended European Search Report for EP 12842668.1-1464 / 2702992 dated May 9, 2014".
"International Search Report for PCT/ES2012/070728 dated Feb. 11, 2013".
Benes, et al., "Transmucosal, Oral Controlled-Releas, and Transdermal Drug Administration in Human Subjects: A Crossover Study with Melatonin", Journal of Pharmaceutical Sciences vol. 86, No. 10, Oct. 1997, 1115-1119.
Blasiak, et al., "Perspectives on the use of melatonin to reduce cytotoxic and genotoxid effects of methacrylate-based dental materials", J Pineal Res. 2011: 51:157-162.
Czesnikiewicz-Guzik, et al., "Melatonin and its Role in Oxicative Stress Related Diseases of Oral Cavity", journal of Physiology and Pharmacology 2007, 58 Supp 3, 5-19.
Kaji, et al., "Radical Scavenging activity of bisbenzylisoquinoline alkaloids and traditional prophylactics agaist chemotherapy-indued oral mucosistis", Journal of Clinical Pharmacy and Therapeutics (2009) 34, 197-205.
Konturek, et al., "Melatonin and its Precursor L-Trytophan Prevent Acute Gastric Mucosal Damage Induced by Aspirin in Humans", Journal of Physiology and Pharmacology 2008, 59, suppl 2, 67-75.
Konturek, et al., "Role of Melatonin in Upper Gastrointestinal Tract", Journal of Physiology and Pharmacology 2007, 58, Suppl 6,23-52.
Lissoni, et al., "Decreased toxicity and increased efficacy of cancer chomotherapy using the pineal hormone melatonin in metastatic solid tumour patients with poor clinical status.", European Journal of Cancer, 1999, vol. 35, No. 12 pp. 1688-1692.
Ozturk, et al., "Histapathological evaluation of the effects of melatonin as a protectant against oropharyngeal mucositis induced by radiation therapy in pinealectomy model in rats", International Journal of Hematology and Oncology, 2009 vol. 19, No. 2, pp. 88-94.
Plevova, et al., "Prevention and treatment of chemotherapy and radiotherapy induced oral mucosistis: a review.", Oral Oncology, 1999, vol. 35, pp. 453-470.
Yeager, et al., "Melatonin as a principal Component of red light therapy.", Medical hypotheses, 2007, vol, 69, pp. 372-376.

*Primary Examiner* — Samantha Shterengarts
(74) *Attorney, Agent, or Firm* — Kramer Amado, P.C.

(57) ABSTRACT

The present invention relates to the use of a composition comprising melatonin or a derivative thereof at a proportion of 2.5% to 5% w/v for preparing a pharmaceutical composition for treating and/or preventing mucositis. The mucositis is preferably caused by radiotherapy and/or chemotherapy and preferably refers to oral mucositis.

17 Claims, 22 Drawing Sheets

CONTROL    IR    IR+1% MT    IR+3% MT    IR+5% MT

IRRADIATED + MT IP

USE OF MELATONIN FOR TREATING AND/OR PREVENTING MUCOSITIS

The present invention relates to the use of a composition comprising melatonin (N-acetyl-5-methoxytryptamine) or its derivatives at a concentration of 2.5% to 5% weight/volume (w/v) for preparing a pharmaceutical composition for treating and/or preventing mucositis. The mucositis is preferably caused by radiotherapy and/or chemotherapy. The invention could therefore be comprised in the field of medicine.

STATE OF THE ART

Treating malignant tumors with radiotherapy or chemotherapy, or the association of both, is increasingly more effective but is associated with short- and long-term side effects. Among these side effects are oral mucosa function and integrity disorders. Consequences include serious ulceration (mucositis) and fungal superinfection of the mouth (candidiasis, thrush). These complications induced by the disease and its treatments involve pain in swallowing, dysphagia, malnutrition, delays in chemotherapy administration, interruptions in the radiotherapy scheme, loss of effectiveness of oncological treatments, prolonged hospital stays, elevated costs and in some patients, potentially deadly infections (sepsis).

Mucositis is an inflammatory reaction affecting the entire gastrointestinal tract, from the mouth to the anus, and it is one of the main adverse effects of chemotherapy and/or radiotherapy and bone marrow transplant. Mucositis can also be caused by chemical agents such as corticoids, immunosuppressive drugs (azathioprine, cyclosporine A), xerostomia-inducing drugs, anxiolytics, antidepressants, antihistamines, sympathomimetic stimulants, antiparkinsonians, antipsychotics, gingival treatments, hydantoins or broad-spectrum antibiotics.

Oral mucositis (or oromucositis) induced by ionizing radiations (also called radiation-induced oral mucositis) and by chemotherapy agents is currently one of the main problems with therapy in cancer patients. 40% of patients receiving chemotherapy and/or radiotherapy, and up to 76% of bone marrow transplant patients, develop buccal problems, the most common buccal problems being: mucositis, local infection, pain and bleeding. 97% of head and neck cancer patients develop some degree of mucositis, and 100% of patients subjected to fractionated radiotherapy for a prolonged time also develop it (Trotti A et al. Radiotherapy and Oncology 2003, 66:253-262). The damage caused by ionizing radiations is due to direct and indirect mechanisms. Direct effects are due to the mutagenic action of radiation in deoxyribonucleic acid (DNA), whereas indirect mechanisms (about 70% of such mechanisms) are due to the effect of radiation on water molecules, giving rise to the formation of free radicals (Trotti A et al. Radiotherapy and Oncology 2003, 66:253-262).

According to the World Health Organization (WHO), mucositis is classified in different grades based on symptomatology. Grade 0: normal; grade 1: generalized erythema, pink, non-painful mucosa with abundant saliva, normal voice; grade 2: erythema, ulcers not very widespread, able to swallow solids; grade 3: erythema, edema or widespread ulcers, the patient can only swallow liquids, painful and difficulty in speaking; grade 4: very widespread ulcers, bleeding gums, infections, no saliva, very intense pain, enteral or parenteral support.

Mucositis occurs as a consequence of a series of biological events that start in the submucosa and progress towards the epithelium and are common for mucositis having different etiologies. It has been described in radiotherapy and chemotherapy that in a first phase there is an increase in reactive oxygen species (ROS) and damage to DNA. Transcription factors such as nuclear factor kappa-B (NF-kB) are activated. There is an increase in the production of proinflammatory cytokines, including interleukin-1 (IL-1) and tumor necrosis factor alpha (TNFα), causing apoptosis and cell damage. This inflammatory reaction produces damage in the mucosa with the consequent onset of ulcers. These cells will be colonized by bacteria, and macrophages producing more cytokines responsible for all tissue damage are activated. In this entire process there is a large increase in free radicals which contribute to increasing the inflammatory process and cell damage. In a second phase, radiotherapy and/or the chemotherapy inhibit the replication of the epithelial cells, reducing cell renewal. In a third phase, bacterial colonization and the ulcerated surface continue to increase, facilitating the onset of a systemic infection (Volpato L E et al. Mol Cancer Ther 2007, 6:3122-3130). Mucositis is an inflammatory pathology that does not respond to treatment with known anti-inflammatories. Mucositis is a process in which a biochemical mechanism different from the rest of the inflammatory processes, such as the inflammasome pathway, could intervene (Escames G, et al. Hum Genet, July 2011, DOI 10.1007/s00439-011-1057). There is currently no treatment which completely reverses mucositis or which completely prevents it from occurring.

A great variety of therapies have been used until now for treating and preventing mucositis without showing results of complete mucositis reversion, for example, treatment with acyclovir, benzydamine, beta-carotene, calcium phosphate, rinses with alopurinol, aloe vera, chlorhexidine, chamomile, etoposide, folinic acid, glutamine, granulocyte-macrophage colony stimulating factor (GM-CSF), nystatin, misonidazole, povidone, pilocarpine, hematotoxyphyllin, prednisone or sucralfate, has been described (Worthington H V et al. Cochrane Database Syst Rev. October 2007, 17; (4) DOI: 10.1002/14651858.CD000978.pub3; Clarkson J E et al., Cochrane Database Syst Rev. August 2010, 4; (8)), DOI: 10.1002/14651858.CD001973.pub4.

There is accordingly a need for a tool that allows completely reversing and preventing mucositis, specifically in patients subjected to radiotherapy and/or chemotherapy.

DESCRIPTION OF THE INVENTION

The present invention describes the use of a composition comprising melatonin or a derivative thereof at a concentration of 2.5 to 5% w/v for preparing a pharmaceutical composition for treating and/or preventing mucositis.

In vivo results of protecting oral mucosa against damage caused by radiotherapy or chemotherapy are shown. The composition of the invention is useful for protecting oral mucosa as well as gastrointestinal mucosa. The present invention demonstrates that lower concentrations than those described in the composition of the invention are not capable of completely reversing mucositis, whereas concentrations equal to or greater than 3% w/v are capable of treating and completely reversing mucositis caused by ionizing radiations. Results of different administration routes are shown, the topical route being the route that offers the best protection against oral mucositis.

Based on what is described, the present invention relates to the use of a composition comprising melatonin or a derivative thereof at a concentration of 2.5% to 5% w/v for preparing a pharmaceutical composition for treating and/or preventing mucositis. Hereinafter it shall be referred to as the "composition of the invention".

"Concentration of 2.5 to 5% w/v" is understood as the composition comprising between 2.5 to 5 grams of melatonin or a derivative thereof in 100 ml of final composition. The abbreviation "w/v" refers to weight/volume or mass/volume (m/v).

A preferred embodiment relates to the use where the concentration of melatonin or of a derivative thereof is 3% w/v. Therefore, said preferred composition refers to a composition comprising 3 grams of melatonin or a derivative thereof in 100 ml of total volume of the composition. Hereinafter it shall be referred to as the "preferred composition of the invention".

Any compound comprised within general formula I, as well as the pharmaceutically acceptable salts, solvates or prodrugs thereof that are useful for preparing a pharmaceutical composition for treating and/or preventing mucositis is understood as "melatonin or a derivative thereof".

The compounds of general formula I refer to:

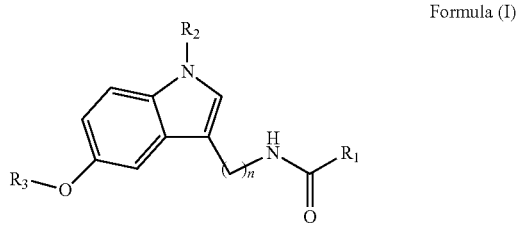

Formula (I)

where:
"n" is an integer between 1 and 4;
$R_1$ and $R_3$ are, identical or different, a linear or branched ($C_1$-$C_4$) alkyl group; and
$R_2$ is hydrogen, linear or branched $C_1$-$C_4$ alkyl, a —C(═O)O—Ra group or a —C(═O)—N(H)—Ra group, wherein Ra is a linear or branched $C_1$-$C_4$ alkyl group.

In the present invention, the term "alkyl" refers to linear or branched aliphatic chains having 1 to 4 carbon atoms, for example, methyl, ethyl, n-propyl, i-propyl, n-butyl, tert-butyl, sec-butyl, n-pentyl, etc. The alkyl group preferably has between 1 and 2 carbon atoms. More preferably it is a methyl group.

In a preferred embodiment of the present invention, $R_1$ and $R_3$ are a methyl group. More preferably n is 1, and even more preferably $R_2$ is hydrogen.

The term "melatonin" refers to N-acetyl-5-methoxy-tryptamine, also referred to in the literature as melatonin, melatonine, melatol, melovine, circadin, regulin, acetamide, N-acetyl-methoxy-tryptamine, 5-methoxy-N-acetyl-tryptamine, N-[2-(5-methoxy-1H-indol-3-yl)ethyl]acetamide or N-[2-(5-methoxyindol-3-yl)ethyl]acetamide, or when $R_1$ and $R_3$ are a methyl group in the compound of general formula (I), n is 1 and $R_2$ is hydrogen. The CAS Registry number for melatonin is 73-31-4.

Melatonin is an endogenous neurohormone that is physiologically produced in animals, including humans, by the pineal gland (epiphysis cerebri) and by other organs, such as the gastrointestinal tract, the retina, lymphocytes and bone marrow cells, for example.

Melatonin is produced in animals, including humans, from serotonin (5-hydroxytryptamine, 5-HT), which in turn derives from the amino acid tryptophan. Therefore, the present invention could also relate to the use of a composition comprising any of the melatonin precursors (5-HT, tryptophan or intermediate metabolites such as N-acetylserotonin, or NAS), at a sufficient concentration so that they are converted into melatonin in the human body at the concentrations described in the present invention, for preparing a pharmaceutical composition for treating and/or preventing mucositis.

Therefore, the present invention also relates to the pharmaceutically acceptable salts of melatonin or of the derivatives thereof which can be generated by means of chemical methods known by the person skilled in the art, for example, by means of a reaction with an acid in water or in an organic solvent or in a mixture of the two. Ether, ethyl acetate, ethanol, isopropanol or acetonitrile can be used as organic solvent. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate and p-toluenesulfonate.

As it is used herein, the term "prodrug" refers to a chemical compound that has experienced chemical derivation, for example a substitution or an addition of an additional chemical group, to modify any of its physicochemical properties, such as solubility or bioavailability, but it does not modify the technical characteristics of the original molecule. A prodrug could be for example an ester, ether or amide derivative. Bioavailability refers to the availability thereof in a specific biological compartment.

According to this invention, the term "solvate" must be understood as that derivative of melatonin having another molecule, for example a polar solvent, bound by means of a non-covalent bond. Examples of such solvates include hydrates and alcoholates, for example methanolates.

The salts, solvates and prodrugs can be prepared by means of methods known in the state of the art. Non-pharmaceutically acceptable salts, solvates or prodrugs are also within the scope of the invention since they can be useful in the preparation of pharmaceutically acceptable salts, solvates or prodrugs.

The composition of the invention or the preferred composition of the invention can also refer to a composition comprising a functional biological equivalent of melatonin at a concentration that is equivalent to that described in the compositions of the invention.

As it is used herein, the term "functional biological equivalent" or "bioequivalent variable" refers to a molecule with the same function as the described molecule that can show slight variations with respect to the described molecule without said variations contributing any added technical effect to said molecule. The present invention therefore relates to melatonin variants having the same function and showing slight variations without said variations contributing any added technical effect to melatonin.

"Concentration that is equivalent" is understood as that concentration necessary for the functional biological equivalent of melatonin producing the same effect as that described in the present invention by the composition of the invention.

Melatonin is also produced in plants. For example, the presence of melatonin has been described in algae, edible plants, grains, fruits, seeds, roots, stems, leaves and medicinal herbs (Paredes S D et al. J Exp Bot 20089, 60(1):57-69). The presence of melatonin has been described in cocoa, grapes, tomatoes, tea, green tea, algae, grains and olives, for example. The source of the melatonin of the composition of the invention can be a plant source. Melatonin from a plant source (also known as phytomelatonin) can be obtained by any method known by the person skilled in the art for such purpose.

The source of melatonin used in the composition of the invention can also be synthetic. Melatonin can be chemically synthesized by means of techniques known by the person skilled in the art for such purpose.

The term "pharmaceutical composition", or "medicinal product", refers to any substance used for preventing, diagnosing, alleviating, treating or curing diseases in humans or animals. In the context of the present invention, it refers to a composition capable of treating and/or preventing mucositis.

In the present invention, "treating and/or preventing" refers both to therapeutic and prophylactic treatment or preventive measures. Those situations that can be treated include those already associated with alterations as well as those in which the alteration is prevented. An "alteration" is any condition that would benefit from treatment with the composition of the invention, as it is described herein.

As it is used herein, the term "mucositis" mainly refers to the disease occurring with inflammation of the mucosae of the gastrointestinal tract, i.e., oral, pharyngeal, esophageal, stomach and intestinal mucosa, and it is characterized by having an impact on mucosa integrity and function that can lead to ulceration and infection therein. Mucositis can be caused by various etiologies, among them radiotherapy treatment, chemotherapy treatment, bone marrow transplant or treatments with drugs.

A preferred embodiment relates to the use where the mucositis is caused by radiotherapy and/or chemotherapy.

Radiotherapy is understood as a treatment based on the use of ionizing radiations capable of ionizing matter, such as x-rays or radioactivity, for example, which includes both gamma rays and alpha particles. The present invention relates to treatment with ionizing radiations used in cancer treatments and including any treatment known by the person skilled in the art that generates mucositis.

Chemotherapy is understood as a treatment based on the administration of an agent that causes tumor growth inhibition and includes any treatment known by the person skilled in the art that generates mucositis. For example, the chemical agent can refer to methotrexate, procarbazine, thioguanine, mercaptopurine, cytarabine, fluorouracil, floxuridine, vinblastine, vincristine, dactinomycin, daunorubicin, doxorubicin, mithramycin, bleomycin, asparaginase or irinotecan.

Another preferred embodiment relates to the use where the mucositis is oral, pharyngeal, esophageal, stomach or intestinal mucositis. Another preferred embodiment relates to the use where the mucositis is oral mucositis.

Another preferred embodiment relates to the use where the mucositis is in humans.

Another preferred embodiment relates to the use where the composition further comprises at least one pharmaceutically acceptable excipient or adjuvant.

The term "excipient" refers to a substance which aids in the absorption of the pharmaceutical composition or medicinal product of the invention, stabilizes said pharmaceutical composition or aids in the preparation thereof in the sense of giving it consistency or providing flavors that make it more palatable. So the excipients could have the function of keeping the ingredients together, such as starches, sugars or celluloses, for example; the function of sweetening; the function of acting as a dye; the function of protecting the medicinal product such as to isolate it from the air and/or moisture, for example; the function as a filler for a pill, capsule or any other presentation form, such as dibasic calcium phosphate, for example; a disintegration function to facilitate dissolving the components and the absorption thereof in the intestine, without excluding excipients of another type not mentioned in this paragraph. An essence, such as for example, cinnamon, lemon, orange, mandarin or vanilla essence, can be added in order for the composition of the invention to have a pleasant taste.

The term "adjuvant" refers to any substance that enhances the response of a drug substance. In the present invention, said term refers to any substance that enhances the effects of the composition of the invention; it can refer to any adjuvant known by the person skilled in the art.

The term "pharmaceutically acceptable" refers to the compound in question being allowed and evaluated such that it does not damage the organisms in which it is administered.

Another preferred embodiment relates to the use where the composition further comprises a gelling agent. The gelling agent is preferably selected from the list comprising polyethylene and polypropylene copolymer, cellulose and guar gum. It preferably refers to polyethylene and polypropylene copolymer. Based on what is described herein, another preferred embodiment relates to the use where the composition is a gel (or also referred to as a "hydrogel").

The term "gelling agent" refers to a substance that forms a gel, i.e., a three-dimensional network formed by the gelling agent, and generally contains a liquid phase. The gelling agent that can be used can be those known by the person skilled in the art for preparing a pharmaceutical composition. For example, out of the polyethylene and polypropylene copolymers, poloxamer copolymers (or poloxamer) could be used, for example the agents called Pluronic®, including Pluronic® F127 (CAS Registry number 9003-11-6) or Pluronic® F127NF.

Another preferred embodiment relates to the use where the composition further comprises at least one preservative.

A preservative is understood as a substance that maintains the properties of the medicinal product by inhibiting germ contamination; it can be an ionic or non-ionic preservative. The preservative used will not be toxic, will be chemically stable and will be compatible with melatonin. The preservatives known in the state of the art can be used as preservatives, for example, preservative can refer to benzoic acid, sodium benzoate, ascorbic acid, potassium sorbate, methylparaben, ethylparaben or butylparaben. "Germs" are understood as any cell that can grow and multiply in the composition of the invention, for example bacteria, fungi and yeasts.

Another preferred embodiment relates to the use where the composition further comprises an antioxidant.

The term "antioxidant" refers to that substance which is capable of delaying or preventing oxidation. Antioxidant agents known in the state of the art can be used as antioxidant agents, for example tocopherol, ascorbic acid, sodium ascorbate, tartaric acid, butylhydroxyanisole, citric acid, vitamin A or vitamin E.

Another preferred embodiment relates to the use where the composition further comprises at least another drug substance.

As it is used herein, the terms "drug substance", "active substance", "pharmaceutically active substance", "active ingredient" or "pharmaceutically active ingredient" refers to any component that may potentially provide pharmacological activity or another different effect on the diagnosis, cure, mitigation, treatment or prevention of a disease, or that may affect the structure or function of the body of human beings or other animals. For example, alopurinol could be used.

Another preferred embodiment relates to the use where the composition further comprises a pharmaceutically acceptable carrier.

A "pharmaceutically acceptable carrier", or pharmacologically acceptable carrier, refers to those substances, or combination of substances, known in the pharmaceutical sector used in preparing pharmaceutical dosage forms and includes but is not limited to solids, liquids, solvents or surfactants. The carrier can be an inert substance or have an action that is similar to any of the compounds of the present invention. The function of the carrier is to facilitate the incorporation of the expression product of the invention as well as other compounds, allow better dosage and administration or to give consistency and form to the pharmaceutical composition. When the presentation form is liquid, the carrier is the diluent. The pharmaceutically acceptable carriers that can be used in the invention may be those known by the person skilled in the art, for example, lysosomes, millicapsules, microcapsules, nanocapsules, sponges, millispheres, microspheres, nanospheres, milliparticles, microparticles and nanoparticles.

The pharmaceutical composition of the invention can be formulated for administration in a variety of forms known in the state of the art. Such formulations can be administered to an animal, and preferably to a mammal, and more preferably to a human, through a variety of routes including but not limited to topical, oral, parenteral, intraperitoneal, intravenous, intradermal, intralesional, intraarterial, intramuscular, intranasal, or subcutaneous route.

Based on what is described herein, another preferred embodiment relates to the use where the composition is in a dosage form suitable for topical, oral, intraperitoneal, intradermal or subcutaneous administration. An even more preferred embodiment relates to the use where the composition is in a dosage form suitable for topical administration.

The term "topical administration" in the present invention refers to the composition being administered on the surface of the mucosa. Administration can be in the mucosa of any part of the digestive tract, preferably in the oral mucosa. The administration of the composition of the invention can be performed using an oral rinse for several minutes, such that the oral mucosa is impregnated, and it can then be ingested in order to impregnate and be in contact with the entire gastrointestinal mucosa.

In the case of topical administration, the formulations that can be used in the composition of the invention can be the following: oil in water emulsions, water in oil emulsions, milks, lotions, gels, pomades, balms, foams, body oils, soaps, bars, pencils, vaporizers, creams, liniments, ointments, sera and mousses. The composition can also be incorporated in solid supports selected from the group consisting of hydrogels, wipes, patches and face masks.

The dosage for obtaining a therapeutically effective amount depends on a variety of factors, such as age, weight, gender or tolerance of the animal, preferably mammal, and more preferably human, for example. In the sense in which it is used herein, the expression "therapeutically effective amount" refers to the pharmaceutically effective amount of composition that produces the desired effect, and it will generally be determined, among others, by the typical characteristics of said pharmaceutical composition and of the therapeutic effect sought.

A preferred embodiment of the invention relates to the use where the administered daily dose is between 37.5 mg and 75 mg. An even more preferred embodiment relates to the use where the administered daily dose is between 45 mg. Another even more preferred embodiment relates to the use where the dose is administered in a regimen of 15 mg 3 times a day.

Throughout the description and claims the word "comprises" and its variants do not seek to exclude other technical features, additives, components or steps. For the persons skilled in the art, other objects, advantages and features of the invention will be deduced in part from the description and in part from the practice of the invention. The following examples and drawings are provided by way of illustration and do not seek to limit the present invention.

EXAMPLES OF EMBODIMENTS OF THE INVENTION

Figure 1:
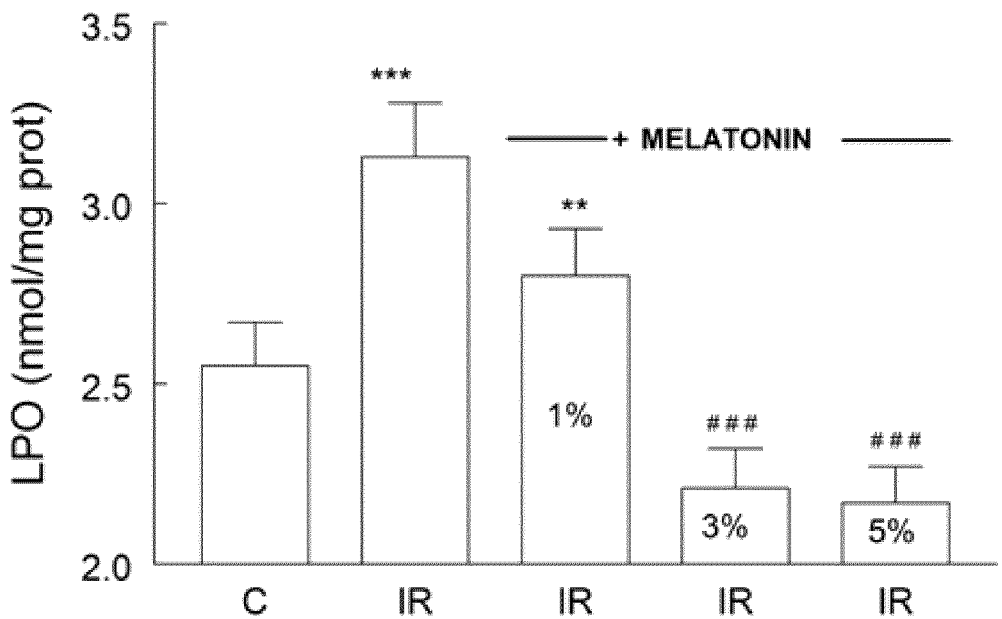
FIG. 1. Oxidative stress levels in a rat tongue homogenate. It shows the results of the lipid peroxidation (LPO) index in control rats, irradiated rats and irradiated rats treated with 1%, 3% or 5% w/v melatonin gel by topical route in the oral cavity. Control group (C); irradiated group (IR); irradiated groups treated with 1%, 3% or 5% melatonin gel. (IR+melatonin). MDA, malonyldialdehyde; 4-HDA, hydroxyalkenal; $p<0.01$ and *$p<0.001$ with respect to C; ####$p<0.001$ with respect to IR.

The following specific examples provided in this patent document serve to illustrate the nature of the present invention. These examples are included only for illustrative purposes and must not be interpreted as limitations to the invention herein claimed. Therefore, the examples described below illustrate the invention without limiting the field of application thereof.

The invention will be illustrated below by means of tests conducted by the inventors, clearly showing the usefulness of melatonin gel in mucositis, and results at different concentrations are shown.

A. Material and Methods

The composition of the invention was administered to animals used in experiments by different administration routes, and experiments with human patients were also conducted.

For topical administration in the oral cavity, the composition used was a hydrogel (gel) that comprised 1%, 3% or 5% melatonin (1, 3 or 5 grams of melatonin in 100 ml of the final volume of the composition, respectively) and in which 20% polyethylene and polypropylene copolymers were used as a gelling substance. Pluronic® F127 (poloxamer) was used as the polyethylene and polypropylene copolymers. 0.3% sodium benzoate was used as a preservative. 0.5% sweet orange essence was used. All the components used were acquired from FAGRON IBERICA, S.A.U., reference numbers: melatonin, 33457-27; Pluronic® F127, 33353-SP; sodium benzoate, 31360-12; orange essence, 30620-08. The chemical structure of melatonin is shown below:

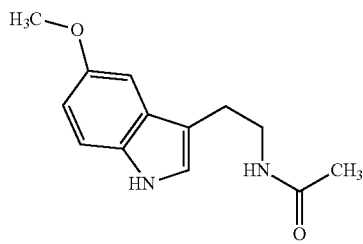 [SMILES: COc1ccc2[nH]cc(CCNC(C)=O)c2c1]

The animals used in experiments were rats weighing 280 g, and they were subjected to ionizing radiations under controlled conditions in the Experimental Radiology Unit at the Biomedical Research Center in the University of Granada. The animals were subjected to full exposure of 50 grays (Gy). The irradiation dose used each day was 10 Gy administered at 100.75 cGy/min, 210 kilovolts (kV) and 12 milliamperes (mA), and placing the animal 40 cm away from the radiation source.

The different formulations were applied to the animals as follows. A topical application was applied in the oral cavity before irradiation, another one after, and successive applications were applied every 8 hours for 21 days. The animals were sacrificed 21 days after starting irradiation, which is when the highest grade of mucositis was observed in irradiated animals not treated with melatonin. The formulations used in the animals used in experiments were as follows: Pluronic F-127 gel with 1%, 3% or 5% melatonin (1, 3 or 5 grams of melatonin/100 ml gel, respectively), applied three times a day topically in the oral cavity at a volume of 500 µl/each time, giving a total of 1.5 ml/day. Topical application in the oral cavity means that the animals ingest the gel applied in the buccal cavity.

The experiments were also conducted by administering to the animals the same melatonin concentration as that used with the 3% w/v hydrogel, but by intraperitoneal route, to see if plasma melatonin could reduce mucositis or if it is necessary to apply said molecule by topical route. For the parenteral route, an isotonic solution that comprised 70% v/v (volume/volume) of isotonic saline solution and 30% v/v of propylene glycol, measured in relation to the total volume of the solution, was used. A daily dose of 45 mg of melatonin was injected for 21 days. The animals were sacrificed 21 days after starting irradiation, like the animals treated with melatonin gel applied by topical route in the oral cavity.

The protective role of the 3% w/v melatonin composition in head and neck cancer patients subjected to radiotherapy was also evaluated. The study was a double blind study (5 patients treated with 3% w/v melatonin gel and 5 patients treated with gel without melatonin). The patients were subjected to oral rinses with the gel described above with 500 microliters three times a day, i.e., the patients received a total of 45 mg/day of melatonin distributed into a regimen of 15 mg 3 times a day. The patients kept the gel with melatonin in their buccal cavity for 2 minutes, and then they ingested it so that the gel could impregnate the entire gastrointestinal mucosa. Two weekly evaluations were performed in a scheduled visit to determine the objective grade of oromucositis (RTOG (Radiotherapy Oncology Group) Objective Toxicity Scale according to the WHO): Grade 0-4.

B. Evaluated Parameters

B.1. Markers of Oxidative Damage

Evaluation of the Oxidation of Cell Membrane and Sub-Cellular Membrane (LPO)

A very important mechanism whereby free oxygen radicals are capable of producing cell damage is by means of lipid peroxidation of both cell and mitochondrial membranes. Lipid peroxidation occurs due to the action of free radicals on the polyunsaturated fatty acids. These modifications in the cell membrane structure cause changes in its physicochemical properties, with an increase in permeability and a progressive loss of functions, which can lead to the subsequent cell death. Measuring degree of lipid peroxidation of membranes has always been considered a very important parameter as an oxidative stress indicator. The lipid peroxidation (LPO) index is provided by quantifying the malonyldialdehyde and 4-hydroxyalkenal (MDA+4-HDA) present in the sample, these being important products from the decomposition of peroxides derived from polyunsaturated fatty acids and related esters. The concentrations of malonyldialdehyde and 4-hydroxyalkenal, as well as the concentration of hydroperoxides, provide a suitable index for lipid peroxidation.

B.2. Evaluation of Antioxidant Defenses

Within the cellular antioxidant system, there is a group of enzymes responsible for detoxifying free radicals in the cell in physiological conditions, these enzymes essentially being:

Glutathione peroxidase (GPx): this enzyme uses reduced glutathione as a cofactor and removes hydrogen peroxide ($H_2O_2$).

Glutathione reductase (GRd): this enzyme reconverts oxidized glutathione, produced by glutathione peroxidase activity, into reduced glutathione.

The ratio obtained as the quotient by dividing oxidized glutathione/reduced glutathione (GSSG/GSH) is also an important ratio in the evaluation of the redox state.

B.3. Evaluation of Markers of Mitochondrial Activity

Mitochondrial dysfunction associated with an increase in the production of free radicals is responsible for cell death. Therefore, measuring the activity of the respiratory chain transport complexes (I, II, III and IV) and the expression of the complexes is fundamental for knowing the degree of mitochondrial damage.

B.4. Mitochondria and Oxidative Stress: Inflammasome Activation:

The production of reactive oxygen species (ROS) increases in mitochondria damaged by irradiation, causing oxidative alterations of the mitochondrial components and mitochondrial transition pore (MTP) opening. Mitochondrial membrane permeation represents an irreversible point in the activation of the programmed cell death pathways ending in apoptosis or necrosis (Schroder K, et al. Cell. 2010; 140:821-832; Latz E, Curr. Opin. Immunol, 2010; 22: 28-33. Epub 2010).

Recent studies show that the mitochondrion also regulates the innate immune response (Kastner D L, et al. Eur J. Immunol. 2010; 40:611-615). It has been observed that the free radicals originating in the mitochondrion are responsible for activating the cellular inflammatory mechanisms, specifically, the so-called inflammasome such as NLRP3 (NOD-like receptor family, pyrin domain containing 3) (Zhou R, et al. Nature 2011; 469:221-226). NLRP3 is a protein complex mediating in the production of immune messenger IL-1beta and in inflammation.

A wide variety of factors can activate the innate immune response, including pathogenic agents or molecules causing cell damage as a result of an increase in stress. When NLRP3 is activated, it forms a multi-protein complex consisting of NLRP3, the adapter molecule ASC (apoptosis-associated speck-like protein containing a caspase recruitment domain), as well as pro-caspase-1. In cellular stress situations, NLRP3 recruits the ASC protein and procaspase 1, which activates caspase-1, causing a series of intracellular reactions including activation of proinflammatory cytokines.

B.5. Inflammatory Response and NF-kB

The nuclear factor kappa B (NF-kB) pathway also participates in the inflammatory response. The difference with inflammasome is that the NF-kB pathway is activated through Toll-like-receptors (TLR) on the membrane, whereas inflammasome is activated through cytosolic NOD-like receptors (Nucleotide Oligomerization Domain-like receptors) (NLRB), NLRB. NF-kB and NLRP3 work together to activate proinflammatory cytokines such as IL-1β. In parallel, this cytokine can induce mitochondrial damage and increase ROS production, and ROS induce damage in mitochondrial DNA (mtDNA) and MTP opening, causing apoptosis.

Furthermore, NF-kB activates the expression of a wide variety of genes involved in the inflammatory response such as cyclooxygenase 2 (COX-2), inducible nitric oxide synthase (iNOS) and vascular adhesion molecules (VCAM-1). Therefore, irradiation causes an increase in proinflammatory molecules that contribute to apoptosis and, therefore, to the onset of mucositis.

B.6. Mechanisms of Apoptosis:

Proteins regulating apoptosis are grouped into antiapoptotic proteins such as Bcl2 (B-cell lymphoma 2) and proapoptotic proteins such as Bax. Therefore, the Bax/Bcl2 ratio is very important ratio because it directly reflects the level of apoptosis. Protein p53 activates DNA repair enzymes to correct the detected damage. Entering apoptosis is the final mechanism of protection, if damage in the DNA is irreparable, in order to prevent proliferation of the cells containing abnormal DNA. p53 activates the expression of proapoptotic genes such as BAX.

Therefore, the consequences of an increased production of mitochondrial ROS, of damage in the mtDNA and of MTP opening involve maintaining the inflammatory process, so treatment targeting inflammasome can be a pathway for the use of new therapies in inflammatory diseases that do not respond to the anti-inflammatories as occurs with radiotherapy-induced mucositis.

C. Example 1

Results Obtained in Rat Tongue

C.1-Use of Melatonin in a 1%, 3%, and 5% w/v Gel by Topical Route in the Oral Cavity Oxidative stress caused by the radiations causes damage in cell membranes, which is reflected by an increase in oxidation of membrane lipids greater than 50% with respect to the control (FIG. 1, $p<0.001$). This damage indicates that radiations injure these tissues causing mucositis. 3% melatonin completely reverses the effects of radiotherapy, whereas 1% melatonin only partially reverses LPO levels. When using a melatonin concentration greater than 3%, such as 5%, it has the same effects as the 3% concentration in counteracting oxidative stress (FIG. 1).

Figure 2:
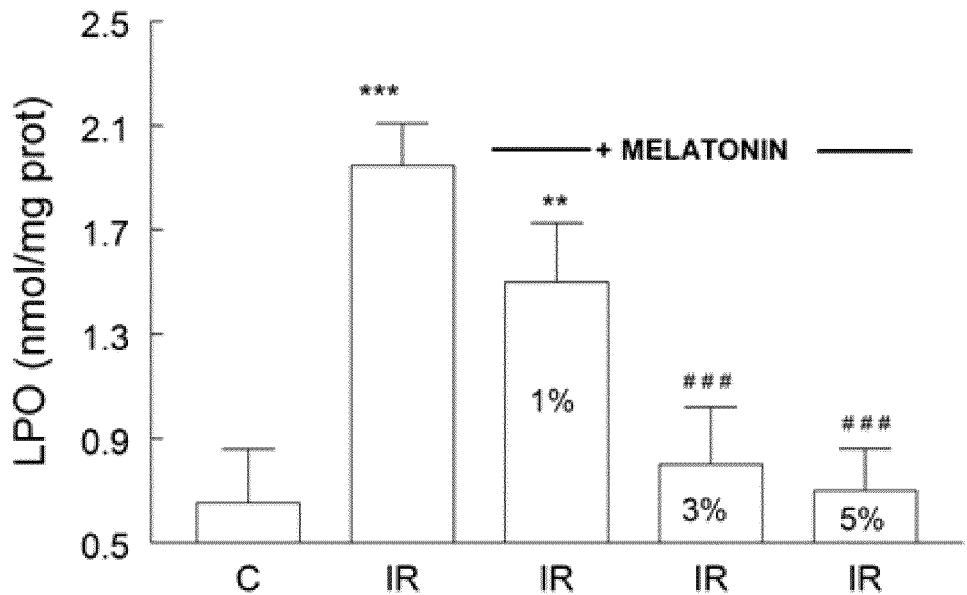
FIG. 2. Oxidative stress levels in rat tongue mitochondria. It shows the results of the lipid peroxidation (LPO) index in control rats, irradiated rats and irradiated rats treated with 1%, 3% or 5% w/v melatonin gel by topical route in the oral cavity. Control group (C); irradiated group (IR); irradiated groups treated with 1%, 3% or 5% melatonin gel (IR+melatonin). MDA, malonyldialdehyde; 4-HDA, hydroxyalkenal; $p<0.01$ and *$p<0.001$ with respect to C; ####$p<0.001$ with respect to IR.

Irradiation also causes intense mitochondrial damage which is reflected by an increase in LPO in mitochondrial membranes (FIG. 2). This mitochondrial damage causes cell death (Acuña-Castroviejo et al. Curr Top Med Chem 2010, 11(2):221-240). When rats irradiated with melatonin are treated, a potent antioxidant effect of melatonin is observed when it is applied at 3%, completely reversing the effects of radiotherapy ($p<0.001$) in the mitochondrion. There is no known currently existing molecule that is capable of exerting these effects. However, when 1% melatonin is applied, it has virtually no effect in counteracting oxidative damage caused by irradiation in the mitochondrion. When using a 5% melatonin concentration, it has the same effects as the 3% concentration in counteracting mitochondrial oxidative stress.

Figure 3:
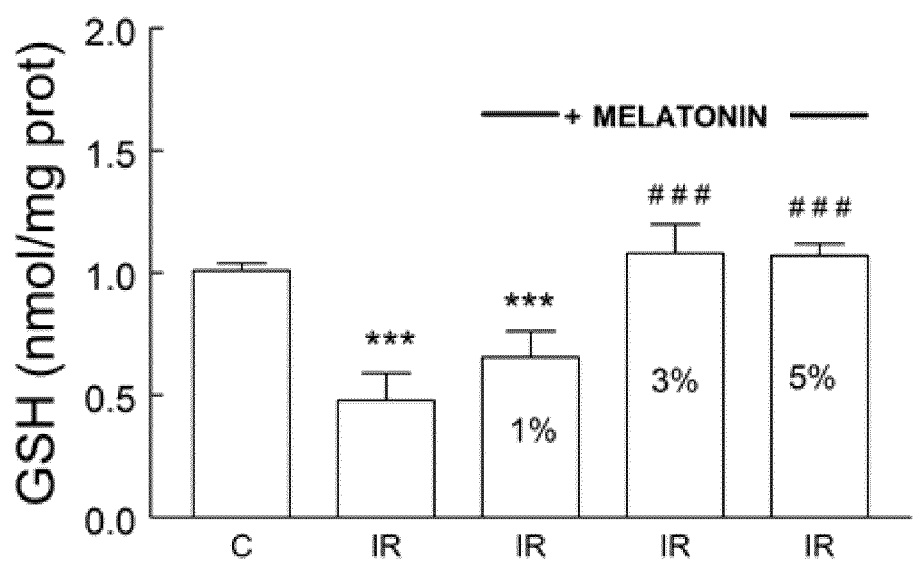
FIG. 3. Glutathione levels in rat tongue. It shows the results of glutathione levels in control rats, irradiated rats and irradiated rats treated with 1%, 3% or 5% w/v melatonin gel by topical route in the oral cavity. A, reduced glutathione levels (GSH); B, oxidized (GSSG); C, total glutathione ($G_T$); D, (GSSG/GSH) ratio in tongue mitochondria from control rats (C), irradiated rats (IR), and rats treated with 1%, 3% and 5% melatonin (IR+melatonin). ***$p<0.001$ with respect to C; ####$p<0.001$ with respect to IR.
Figure 3:
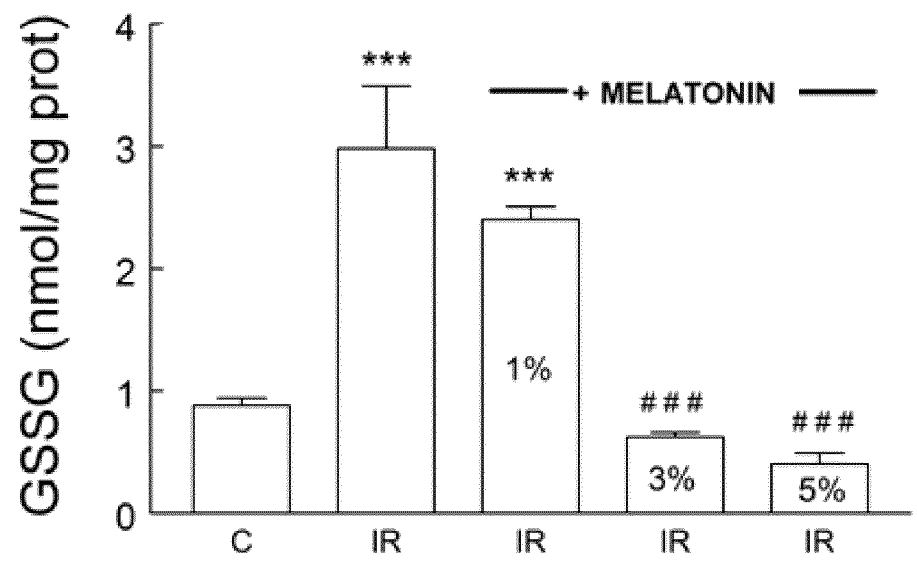
Figure 3:
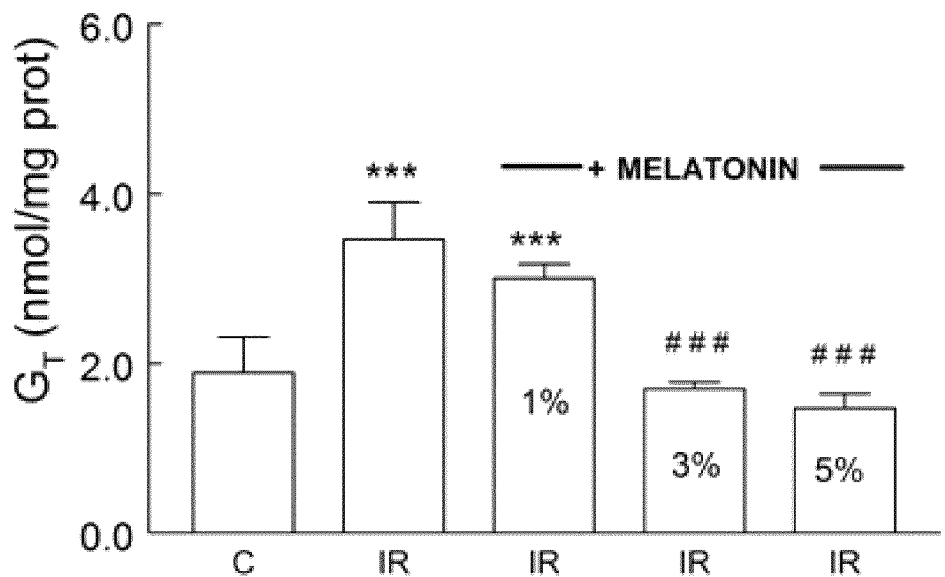
Figure 3:
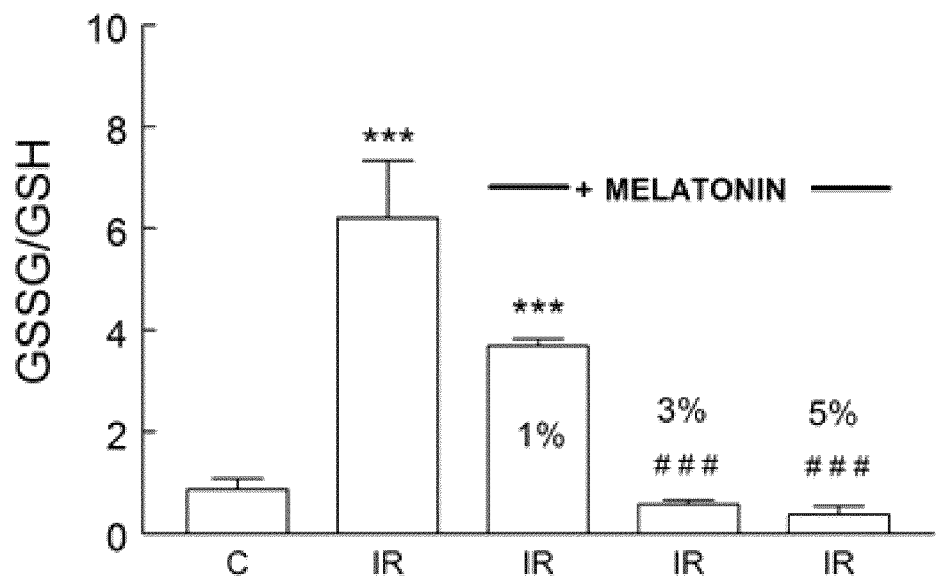

Irradiation also causes a very significant decrease in GSH levels ($p<0.001$) (FIG. 3A), while at the same time GSSG levels ($p<0.001$) increase (FIG. 3B) in the tongue mitochondria, causing an increase in total glutathione (GSH+GSSG) (FIG. 3C). These changes reflect a considerable increase in mitochondrial oxidative stress, which is a reflection of the adverse effects caused by irradiation. The increase in the GSS/GSH ratio ($p<0.001$) (FIG. 3D), which is the best index of intracellular, and in this case intramitochondrial, oxidative stress, supports such harmful effect of irradiation. In turn, the administration of 1% melatonin cannot increase GSH levels (FIG. 3A) and reduce GSSG levels (FIG. 3B), nor can it normalize the GSSG/GSH ratio (FIG. 3D) and therefore neutralize oxidative stress. When using a 5% melatonin concentration, it is observed to have the same effects as the 3% concentration in counteracting mitochondrial oxidative stress, completely reversing the effect of irradiation in both cases.

Figure 4:
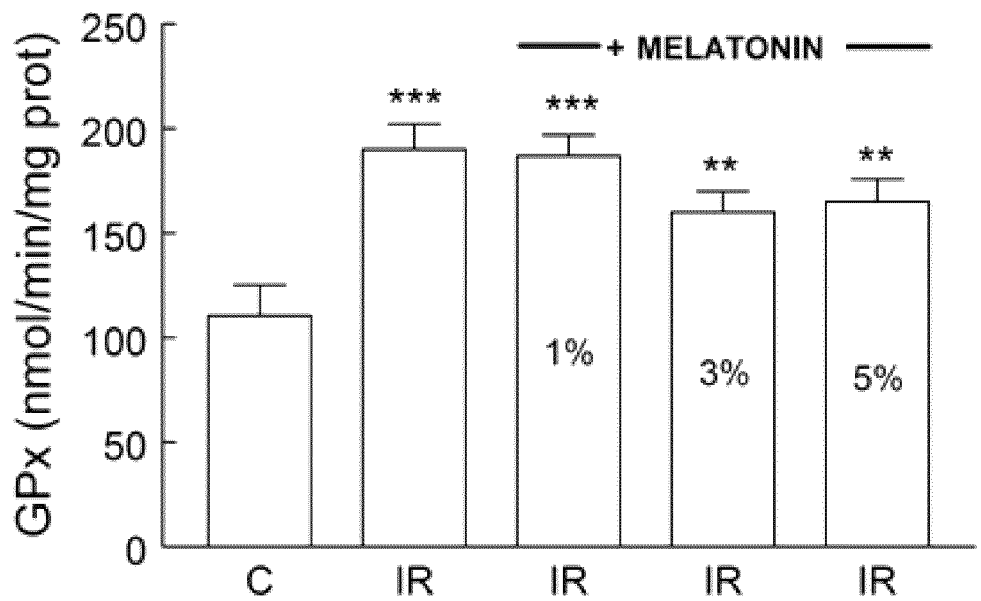
FIG. 4. Activity of glutathione peroxidase and glutathione reductase in rat tongue mitochondria. It shows the results of the activity of: A, glutathione peroxidase (GPx); and B, glutathione reductase (GRd), both in control rats, irradiated rats and irradiated rats treated with 1%, 3% or 5% melatonin gel. Control rats (C), irradiated rats (IR), and irradiated rats treated with 1%, 3% and 5% w/v melatonin gel by topical route in the oral cavity (IR+melatonin). $p<0.01$ and *$p<0.001$ with respect to C; ####$p<0.001$ with respect to IR.
Figure 4:
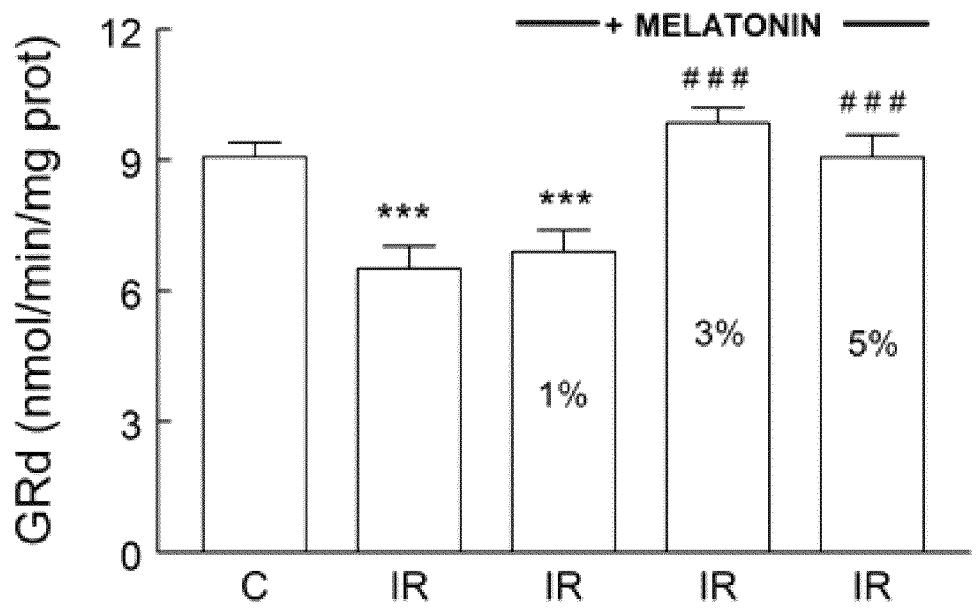

When measuring the activity of glutathione peroxidase (GPx) (FIG. 4A), an increase in activity caused by irradiation as a response to an increase in the peroxides produced is observed. Administration of 3% melatonin gel partially counteracts the effects of irradiation. 5% melatonin has the same effects as the 3% concentration, whereas the 1% concentration has no effect.

When measuring the activity of glutathione reductase (GRd) (FIG. 4B), it is likewise observed that 5% melatonin has the same effect as the 3% concentration, whereas the 1% concentration has no effect. Mitochondrial GRd is an enzyme easily inhibited by oxidative stress, and as a result its activity significantly decreases with irradiation (FIG. 4B, $p<0.001$), an effect which is counteracted by administration of both 3% and 5% melatonin ($p<0.001$).

Figure 5:
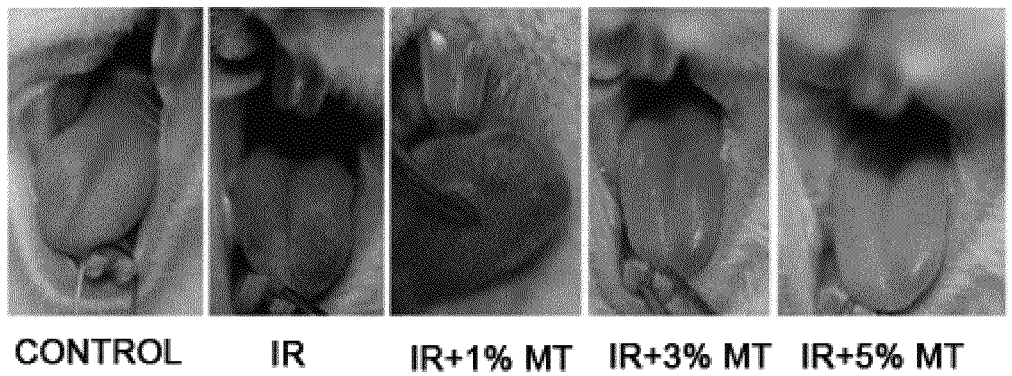
FIG. 5. Macroscopic appearance of the rat tongue after treatment with the composition of the invention. It shows the macroscopic results of the tongue of control rats, irradiated rats and irradiated rats treated with 1%, 3% or 5% w/v melatonin gel by topical route in the oral cavity. Control rats, irradiated rats (IR), and irradiated rats treated with 1%, 3% and 5% melatonin gel (IR+1% MT; IR+3% MT, and IR+5% MT, respectively).

The importance of these actions of melatonin is based on the fact that in addition to the aforementioned biochemical changes, the reduction of mitochondrial oxidative stress translates into complete prevention of mucositis, no other type of lesion being observed in treated rats (FIG. 5). Images of the animals treated with 1% melatonin gel are not included since said concentration had no effect.

Therefore, the minimum effective dose for treating mucositis corresponds to a 3% melatonin concentration in the gel applied three times a day (500 μl in each application), resulting in a daily dose of 45 mg of melatonin.

C.2-Comparison Between the Application of 3% w/v Melatonin Gel and the Administration of the Same Melatonin Concentration by Parenteral Route To determine the most suitable administration route for reversing mucositis, administration of 3% melatonin gel by topical route in the oral cavity and administration of melatonin by intraperitoneal route (i.p.) at the same dose (45 mg a day) were compared.

Figure 6:
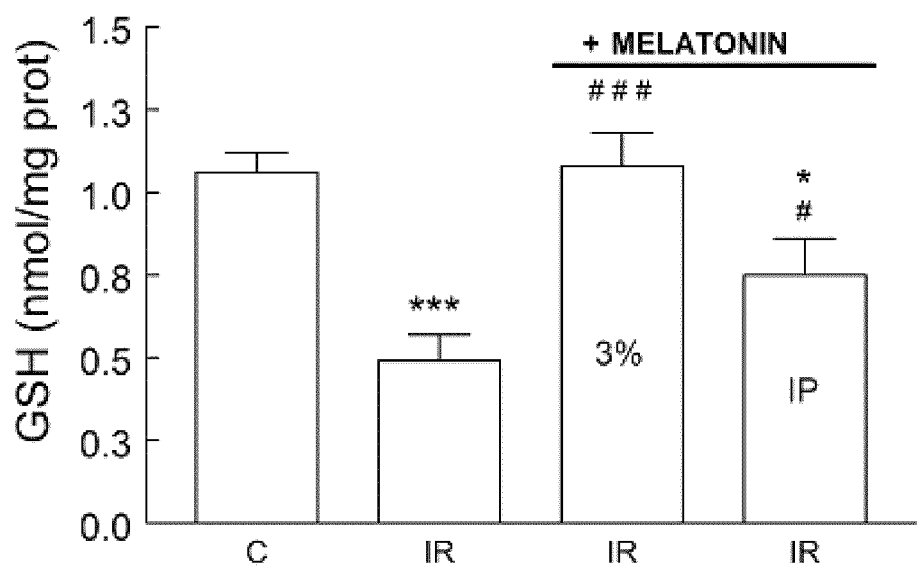
FIG. 6. Comparison between topical administration and intraperitoneal administration with respect to glutathione levels in rat tongue. It shows the results of glutathione levels in control rats, irradiated rats and irradiated rats treated with 3% w/v melatonin by topical route or 3% w/v melatonin by intraperitoneal (i.p.) route. A, reduced glutathione levels (GSH); B, oxidized glutathione levels (GSSG); C, total glutathione levels ($G_T$); D, and GSSG/GSH ratio in rat tongue mitochondria. Control rats (C), irradiated rats (IR), rats treated with 3% melatonin gel (IR+3%), and rats treated with melatonin by i.p. route (IR+IP). ***$p<0.001$ with respect to C; ##$p<0.01$ and ####$p<0.001$ with respect to IR.
Figure 6:
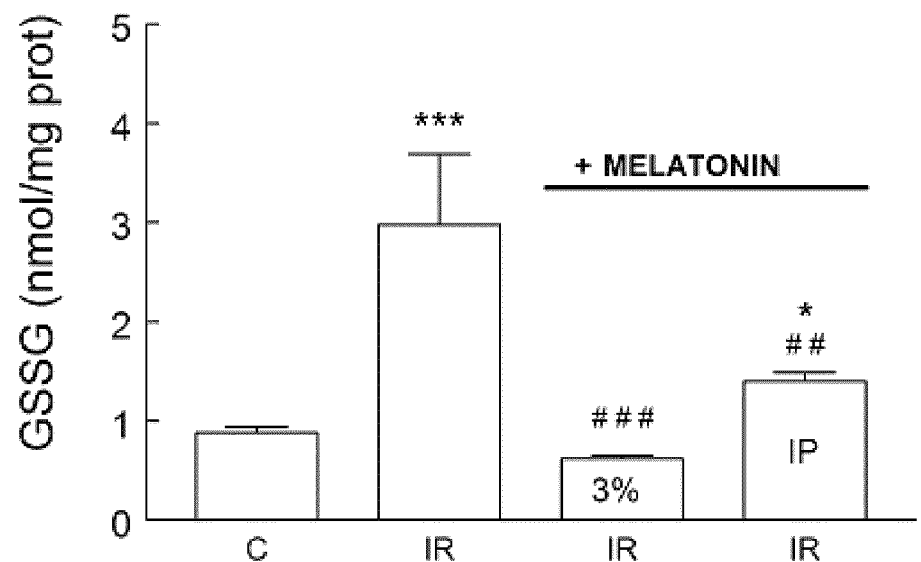
Figure 6:
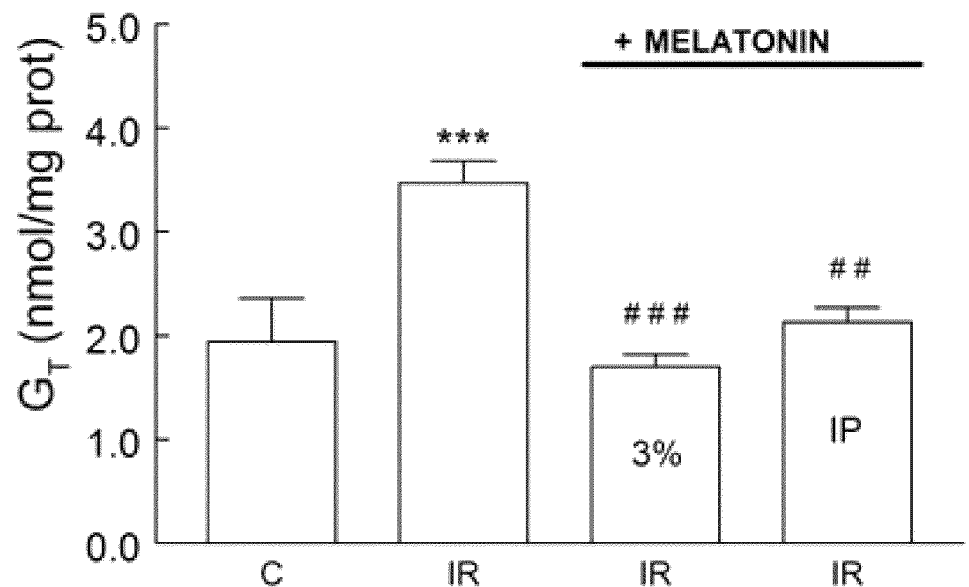
Figure 6:
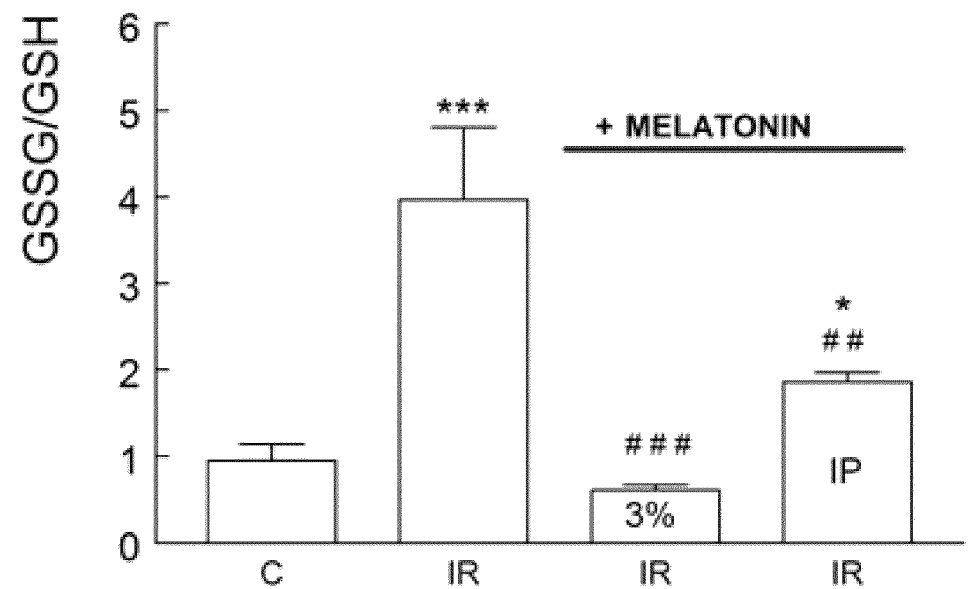

It is observed that the effects of melatonin administered with gel and the administration of melatonin by parenteral route differ in several key aspects, such as lower efficacy of i.p. administration in restoring GSH and in reducing GSSG, which maintains a higher GSSG/GSH ratio, indicating greater intramitochondrial oxidative stress than after applying the gel (FIG. 6). FIG. 6 compares glutathione levels in rat tongue in rats treated with 3% gel and treated with melatonin by intraperitoneal route.

Figure 7:
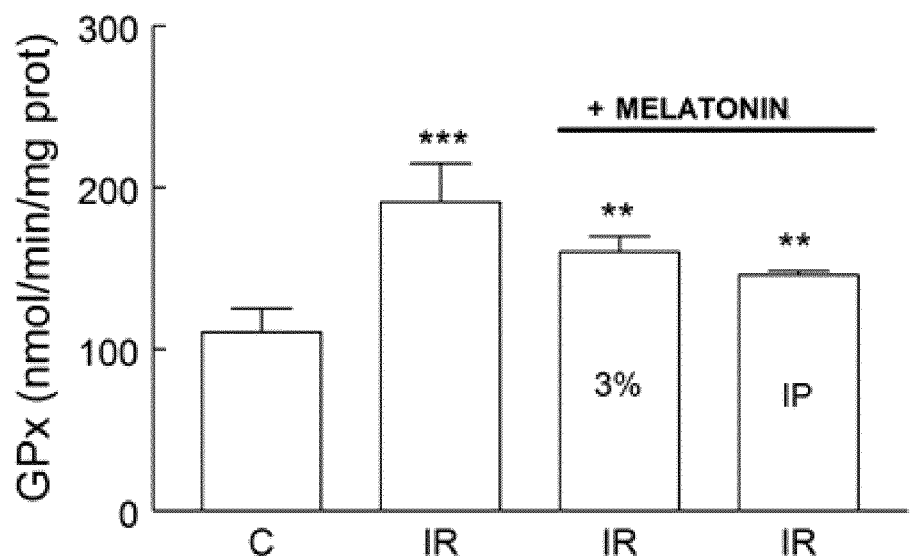
FIG. 7. Activity and expression of GPx in rat tongue in irradiated rats treated with melatonin gel by topical route in the oral cavity and with melatonin by intraperitoneal route. A, GPx activity; B, Western blot densitometry analysis of GPx. C, Western blot image of GPx in tongue mitochondria from control rats (C), irradiated rats (IR), rats treated with 3% w/v melatonin gel by topical route in the oral cavity (IR+3%), and treated with 3% w/v melatonin by i.p. route (IR+IP). p<0.01 and *p<0.05 with respect to C; ##p<0.01 and ####p<0.001 with respect to IR.
Figure 7:
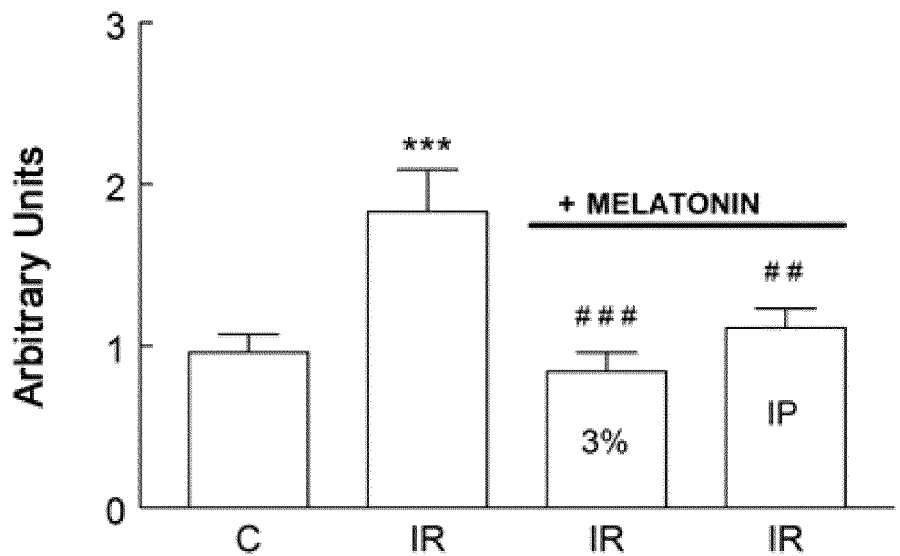
Figure 7:

With respect to mitochondrial glutathione peroxidase (GPx) (FIG. 7) the results indicate an increase in activity (FIG. 7A) and in expression of the enzyme (FIGS. 7B and 7C) due to irradiation, as a response to the increase in peroxides produced. Protein expression studies are conducted by means of Western blot (7C), and an increase in the amount of protein is observed in the densitometry analyses of these Western blots (FIG. 7B), indicating an increase in the expression of said enzyme with irradiation. Both topical administration and intraperitoneal administration of melatonin partially counteract the effect of irradiation.

Figure 8:
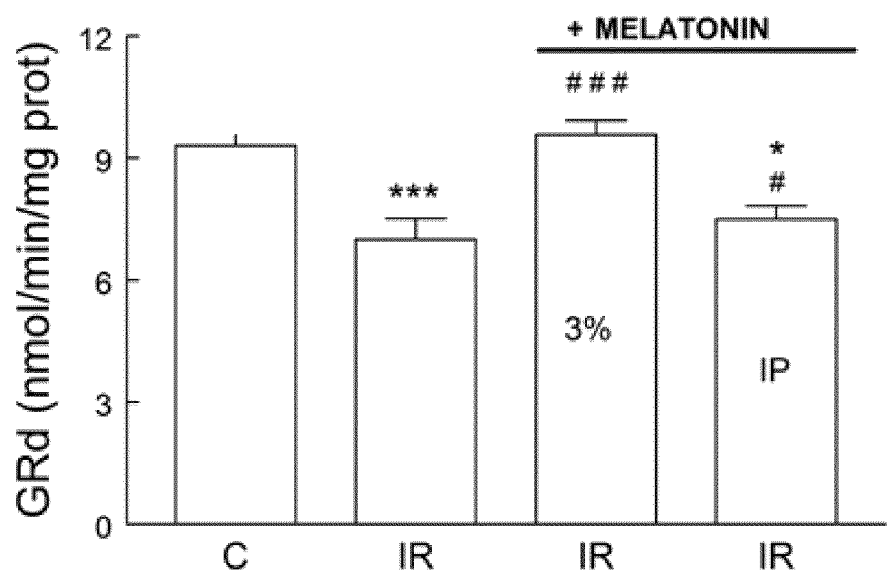
FIG. 8. Activity and expression of GRd in rat tongue in irradiated rats treated with melatonin gel by topical route in the oral cavity and with melatonin by intraperitoneal route. A, GRd activity; B, Western blot densitometry analysis of GRd and C, Western blot image of GRd in tongue mitochondria from control rats (C), irradiated rats (IR), rats treated with 3% w/v melatonin gel by topical route in the oral cavity (IR+3%), and treated with 3% w/v melatonin by i.p. route (IR+IP) ***p<0.001 with respect to C; #p<0.05 and ####p<0.001 with respect to IR.
Figure 8:
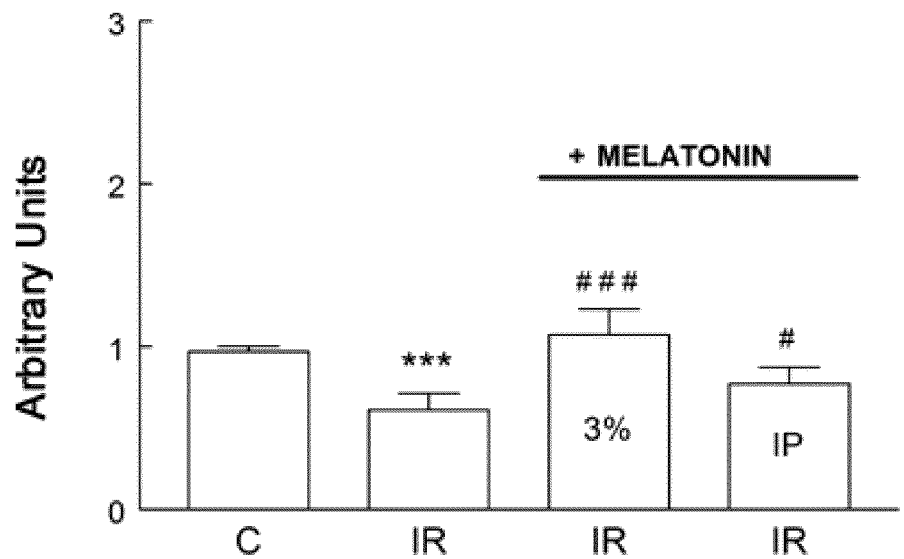
Figure 8:

Mitochondrial glutathione reductase (GRd) (FIG. 8) follows a completely difference path. It is an enzyme easily inhibited by oxidative stress, and as a result its activity (FIG. 8A) and expression (FIGS. 8B and 8C) significantly decrease with irradiation. Protein expression studies are conducted by means of Western blot (8C), and a decrease in the amount of protein with irradiation is observed in the densitometry analyses of these Western blots (FIG. 8B), indicating inhibition of the expression of said enzyme. A significant effect of melatonin gel to restore the activity and expression of GRd is observed, whereas intraperitoneal administration of melatonin is unable to restore the enzyme. If GRd remains inhibited, the mitochondrion is unable to counteract oxidative damage and favors cell death.

Figure 9:
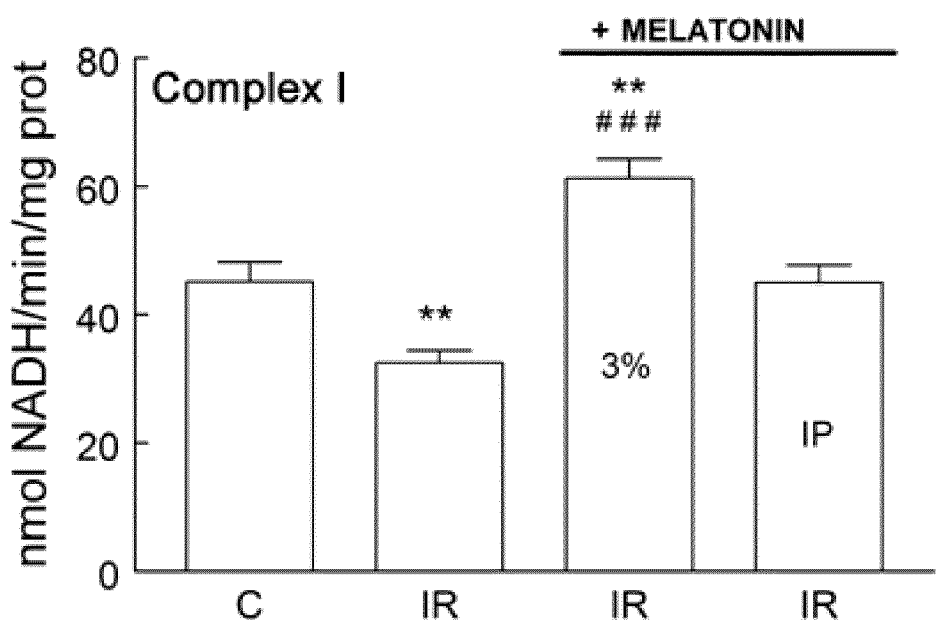
FIG. 9. Activity of mitochondrial respiratory chain complexes CI, CII, CIII and CIV in tongue mitochondria in irradiated rats treated with melatonin gel by topical route in the oral cavity and with melatonin by intraperitoneal route. A, complex I; B, complex II; C, complex III; D, complex IV. Control rats (C), irradiated rats (IR), rats treated with 3% w/v melatonin gel by topical route in the oral cavity (IR+3%), and treated with 3% w/v melatonin by i.p. route (IR+IP). *p<0.05, p<0.01, and *p<0.001 with respect to C; #p<0.05, and ####p<0.001 with respect to IR.
Figure 9:
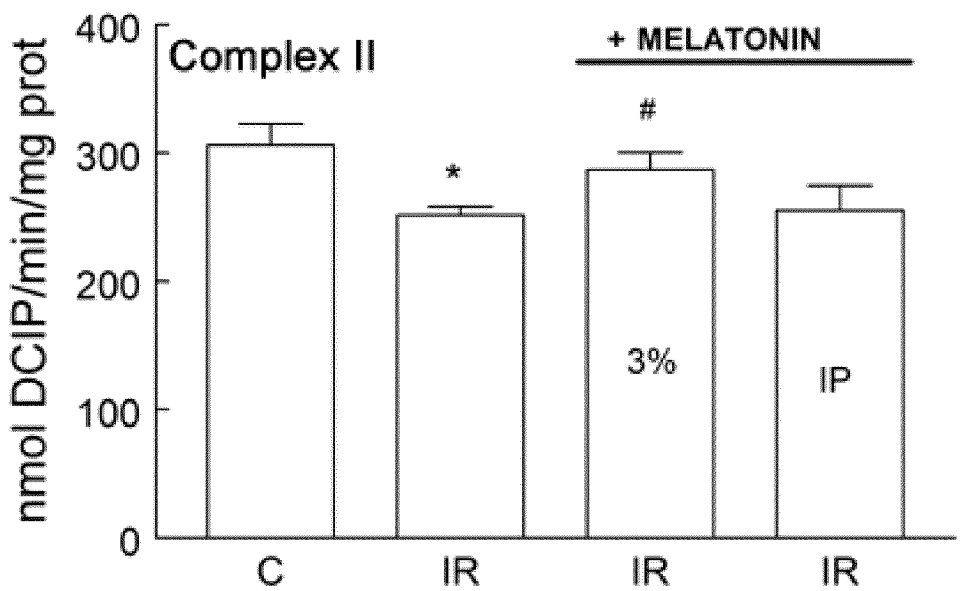
Figure 9:
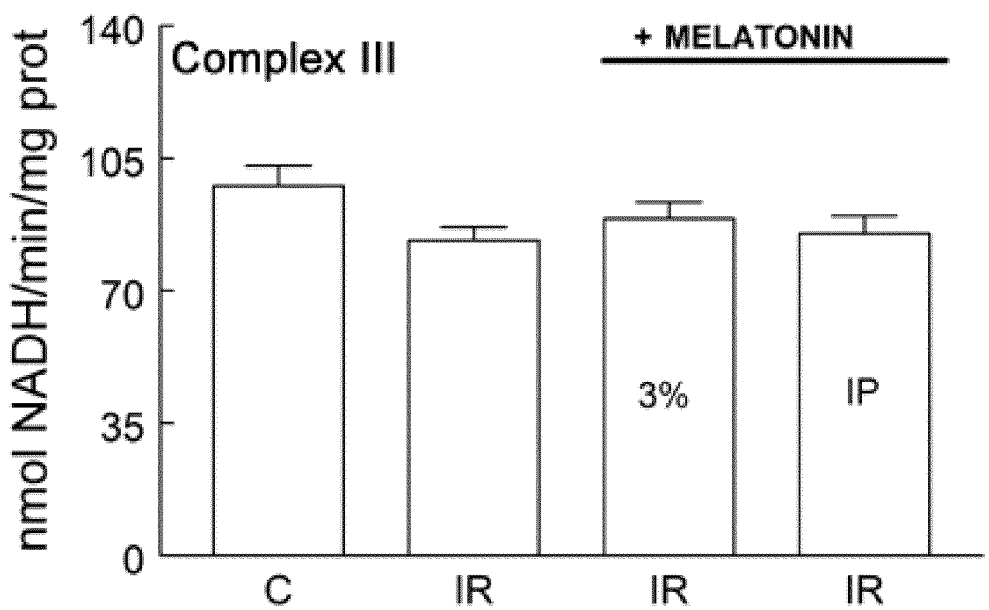
Figure 9:
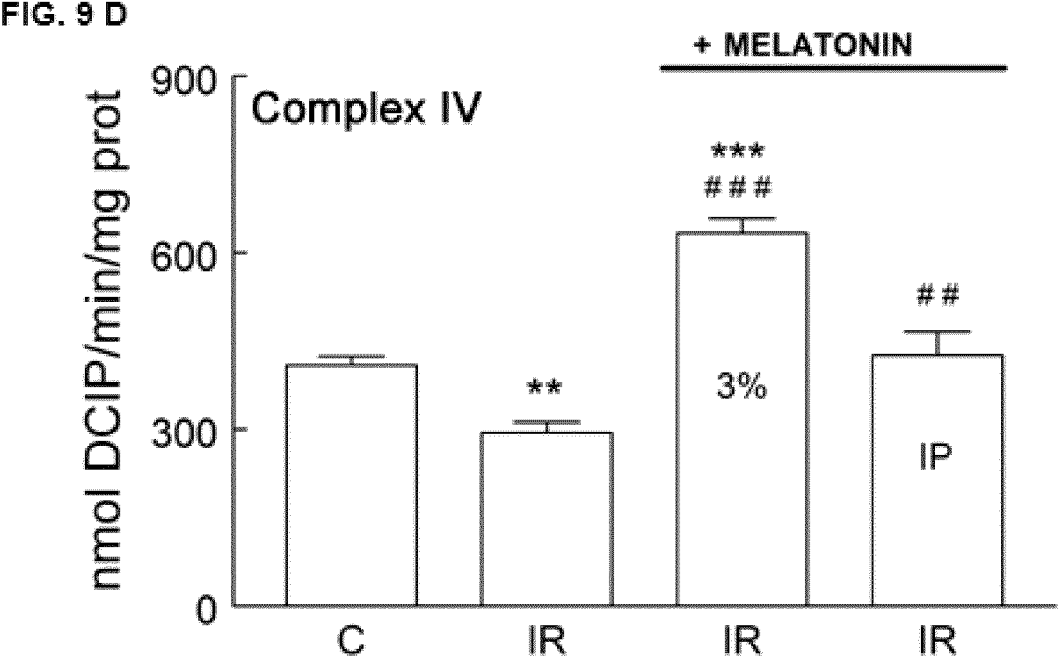

Irradiation causes inhibition of mitochondrial electron transport chain complexes, fundamentally complex I, II and IV (FIGS. 9A, 9B and 9D). No significant changes in complex III (FIG. 9C) are observed. When respiratory chain complexes are damaged, more free radicals are generated, respiratory chain efficiency decreases, less ATP is produced, apoptotic factors are activated and apoptosis increases. Melatonin gel is more efficient in restoring activity of complexes than parenteral administration is, even increasing activity above control values (FIG. 9).

Figure 10:
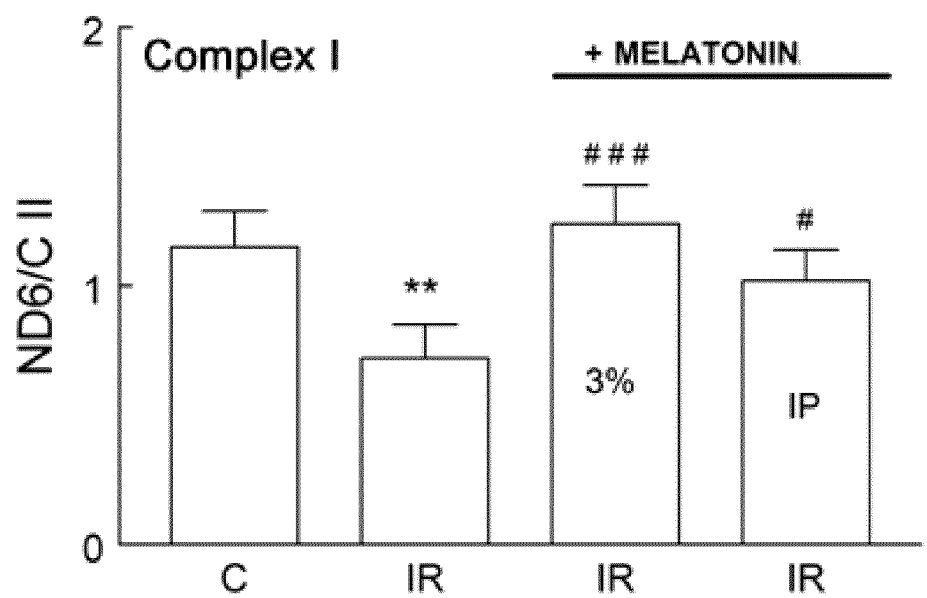
FIG. 10. Expression of mitochondrial respiratory chain complexes CI, CIII, CIV and CV in the tongue by means of Western blot in irradiated rats treated with 3% melatonin gel and with melatonin by intraperitoneal route. A, Western blot band densitometry corresponding to complex I; B, to complex III; C, to complex IV; D, to complex V. E. Western blot image corresponding to complexes I, III, IV and V. Control rats (C), irradiated rats (IR), rats treated with 3% w/v melatonin gel by topical route in the oral cavity (IR+3%), and treated with 3% w/v melatonin by i.p. route (IR+IP). *p<0.05, p<0.01, and *p<0.001 with respect to C; #p<0.05 and ####p<0.001 with respect to IR.
Figure 10:
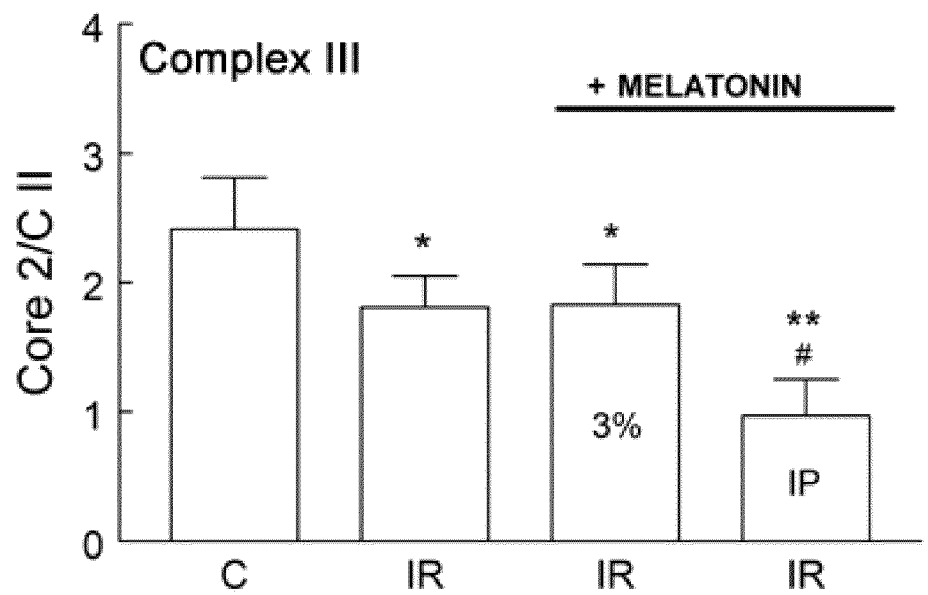
Figure 10:
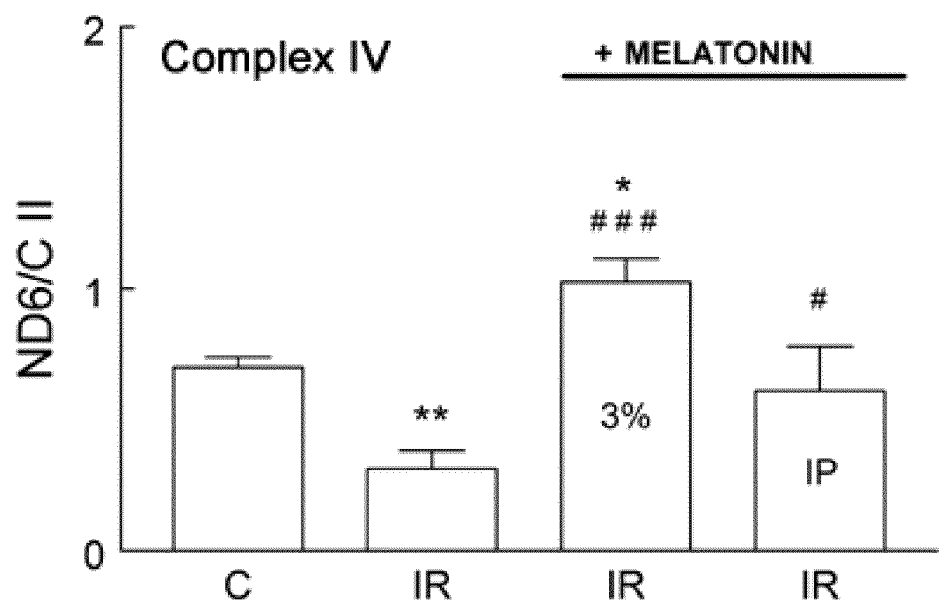
Figure 10:
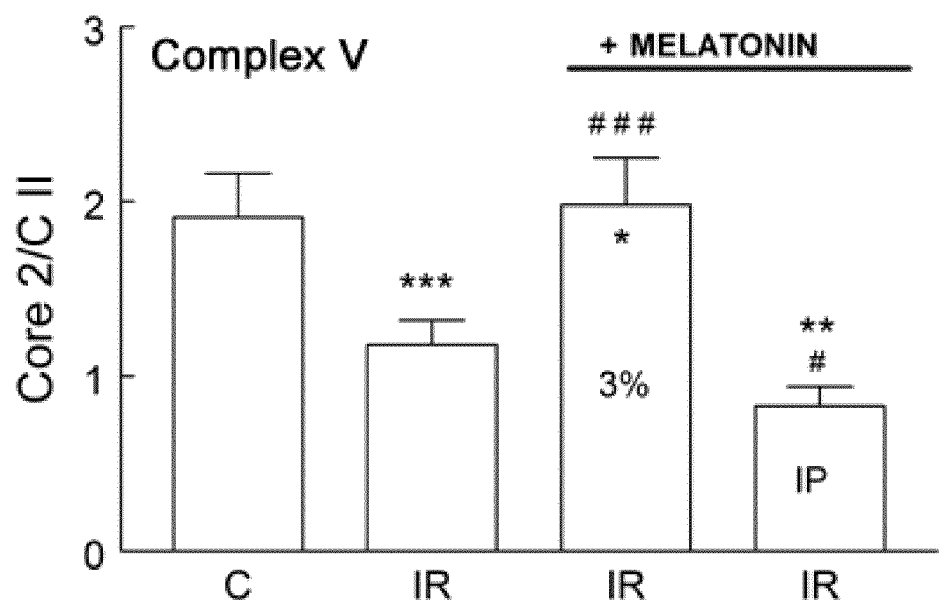
Figure 10:
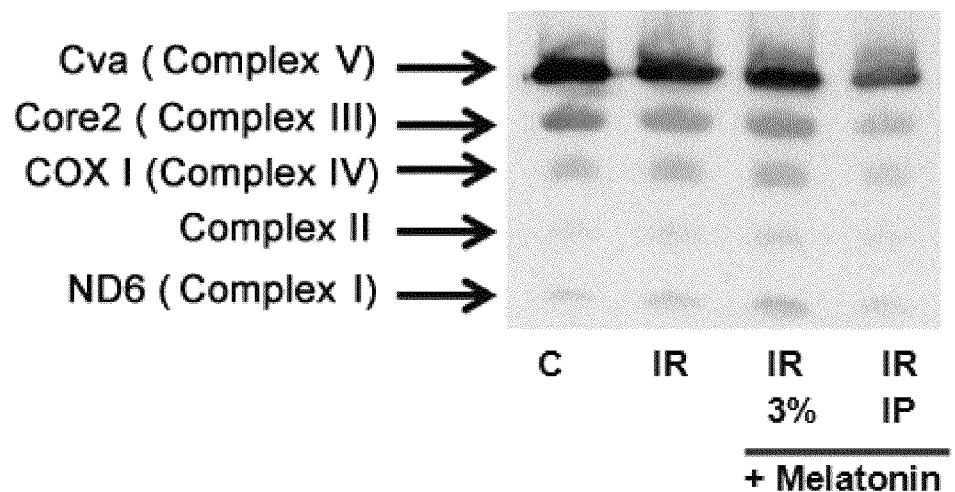

As occurs with activity, irradiation also inhibits expression of the respiratory chain complexes, the inhibition of expression of complexes I, III, IV and V (FIGS. 10A, 10B, 10C, 10D and 10E) being very significant. Western blot studies show a decrease in the amount of proteins of complexes I, III, IV and V, indicating a decrease in synthesis of these complexes with irradiation. Melatonin gel is much more efficient in restoring the expression of complexes than parenteral administration is. It can further be observed that the parenteral application is completely unable to restore the expression of complex V or ATP synthase, the enzyme responsible for ATP synthesis (FIG. 10D). This data is very relevant because if complex V is inhibited, there is no ATP synthesis, and the cell therefore dies due to apoptosis or necrosis (Escames G, et al. Hum Genet, July, 2011, DOI 10.1007/s00439-011-1057). The 3% gel composition is significantly better than the parenteral route in reactivating expression of respiratory chain complexes according to the results shown.

Figure 11:
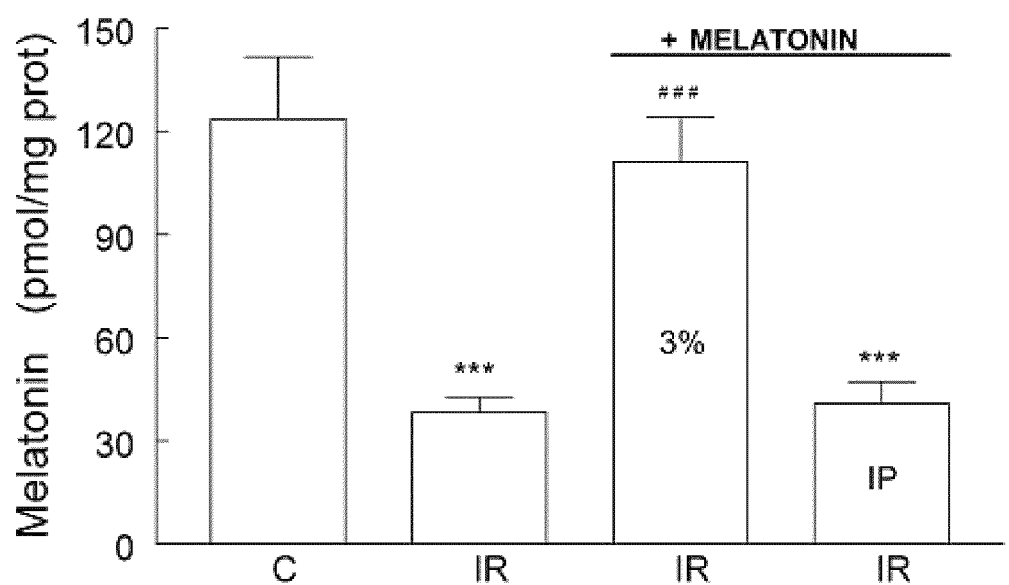
FIG. 11. Melatonin levels in rat tongue mitochondria in irradiated rats treated with melatonin gel by topical route in the oral cavity and with melatonin by intraperitoneal route. Control rats (C), irradiated rats (IR), irradiated rats treated with 3% w/v melatonin gel by topical route in the oral cavity (IR+3% aMT), and irradiated rats treated with 3% w/v melatonin administered by i.p. route (IR+IP). ***p<0.001 with respect to C; ####p<0.001 with respect to IR.

It was found that irradiation suppresses endogenous melatonin levels in the tongue. Said levels are restored with administration of the composition of the invention by topical route in the oral cavity, favoring local antioxidant action. However, such levels are not restored in the tongue with parenteral administration of melatonin (FIG. 11). These results explain why topical administration is much more efficient than parenteral administration of melatonin.

Figure 12:
FIG. 12. Macroscopic appearance of rat tongue after treatment with the composition of the invention by intraperitoneal route. The macroscopic result of the rat tongue in an irradiated rat treated with 3% w/v melatonin and by intraperitoneal route is shown.

These differences in efficiency regarding the action of melatonin according to the administration route are clearly observed upon analyzing macroscopic lesions (FIGS. 5 and 12). In fact, parenteral administration of melatonin is unable to restore tongue lesions after irradiation, whereas topical application in the oral cavity completely normalizes the morphological appearance of the tongue.

Figure 13:
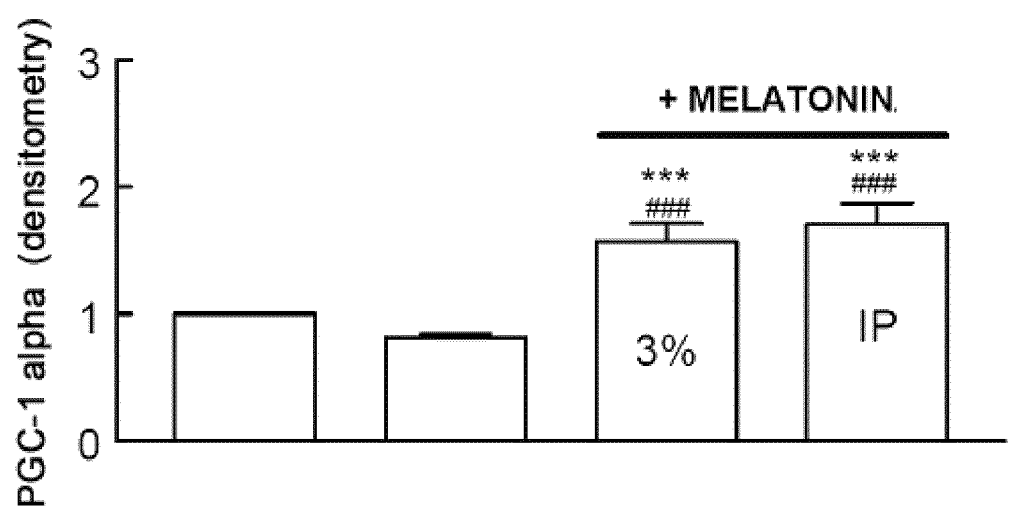
FIG. 13. Expression of PGC-1α, NRF1 and TFAM by means of Western blot in a rat tongue homogenate from irradiated rats treated with melatonin gel by topical route in the oral cavity and with melatonin by intraperitoneal route. A, Western blot band densitometry corresponding to PGC-1α; B, to NRF1; C, to TFAM; D, Western blot image corresponding to PGC-1α, NRF1 and TFAM. Control rats (C), irradiated rats (IR), rats treated with 3% melatonin gel (+3% aMT) and treated with melatonin by i.p. route (+IP aMT). *p<0.05, p<0.01 and *p<0.001 with respect to C; ####p<0.001 with respect to IR.
Figure 13:
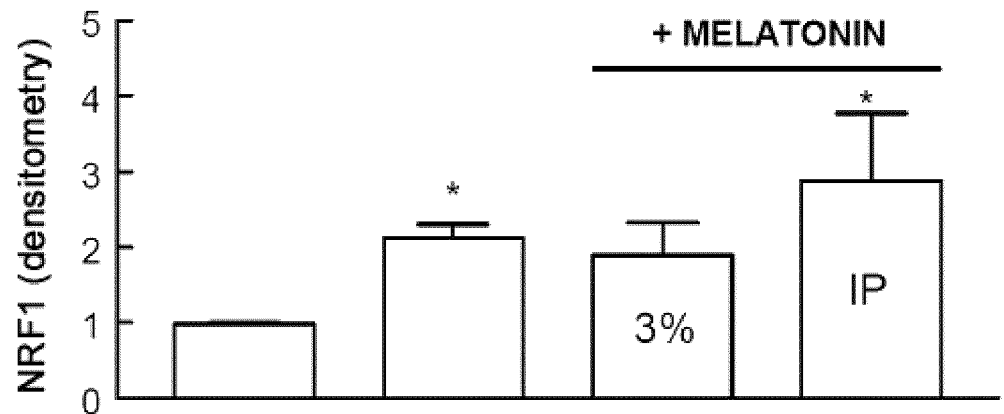
Figure 13:
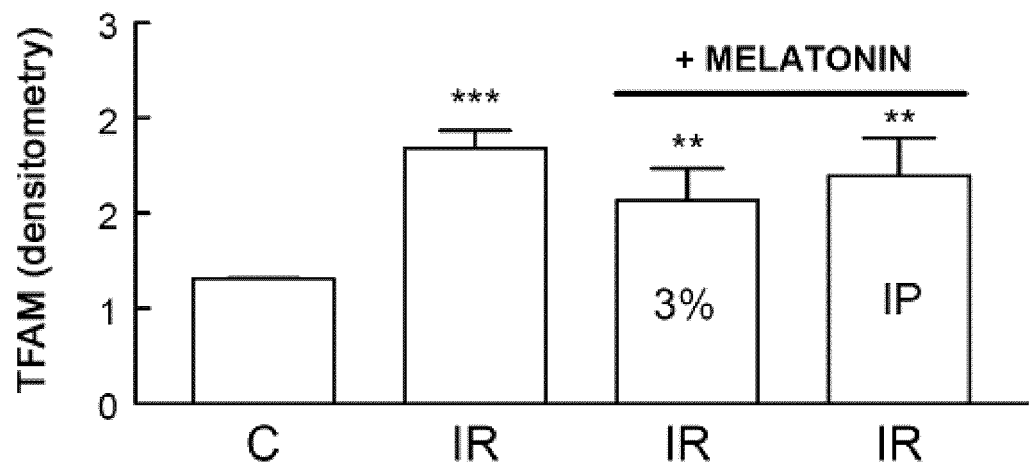
Figure 13:
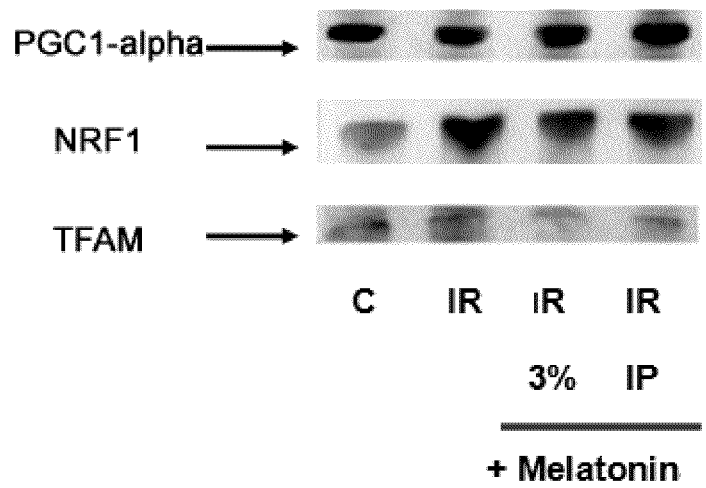

C.3-Data about Inflammasome Activation, Inflammatory Response and Mechanisms of Apoptosis When measuring mitochondrial biogenesis by measuring PGC1α (Peroxisome proliferator-activated receptor gamma co-activator 1-alpha), NRF1 (Nuclear respiratory factor 1) and TFAM (Transcription factor A, mitochondrial), it is observed that irradiation inhibited PGC1α, however there was an increase in NRF1 and TFAM to make up for mitochondrial damage (FIG. 13).

Figure 14:
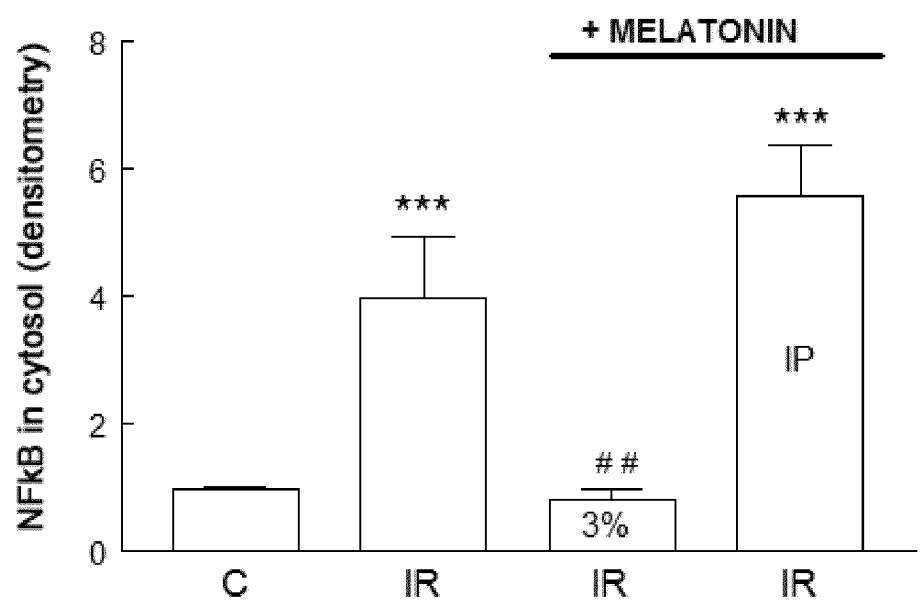
FIG. 14. Expression of NFkB by means of Western blot in rat tongue in irradiated rats treated with melatonin gel by topical route in the oral cavity and with melatonin by intraperitoneal route. A, Western blot band densitometry corresponding to NFkB in the cytosol; B, NFkB in the nucleus; C, Western blot image corresponding to NFkB in the cytosol and NFkB in the nucleus. Control rats (C), irradiated rats (IR), rats treated with 3% melatonin gel (+3% aMT), and treated with melatonin by i.p. route (+IP aMT). *p<0.001 and p<0.01 with respect to C; ###p<0.01 with respect to IR.
Figure 14:
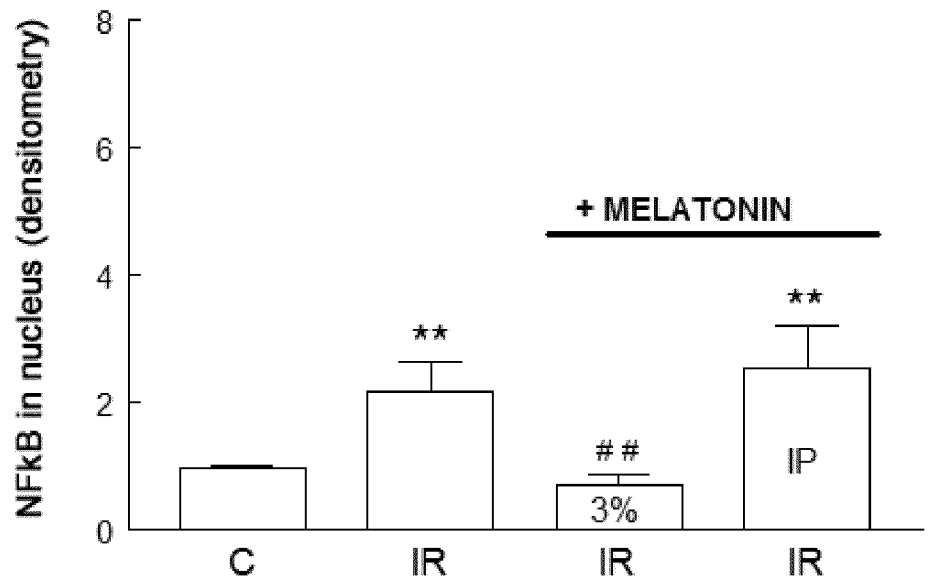
Figure 14:
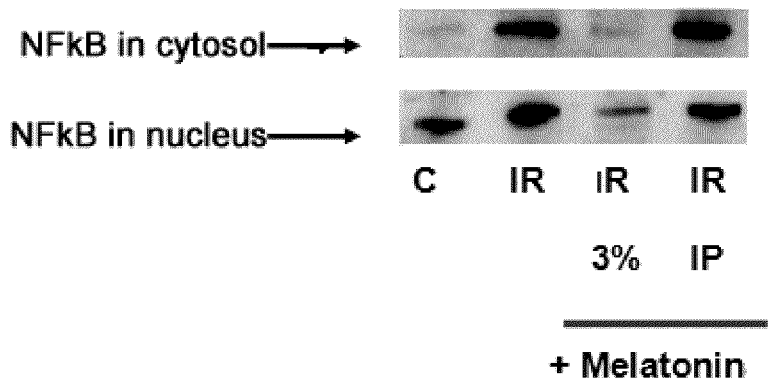
Figure 15:
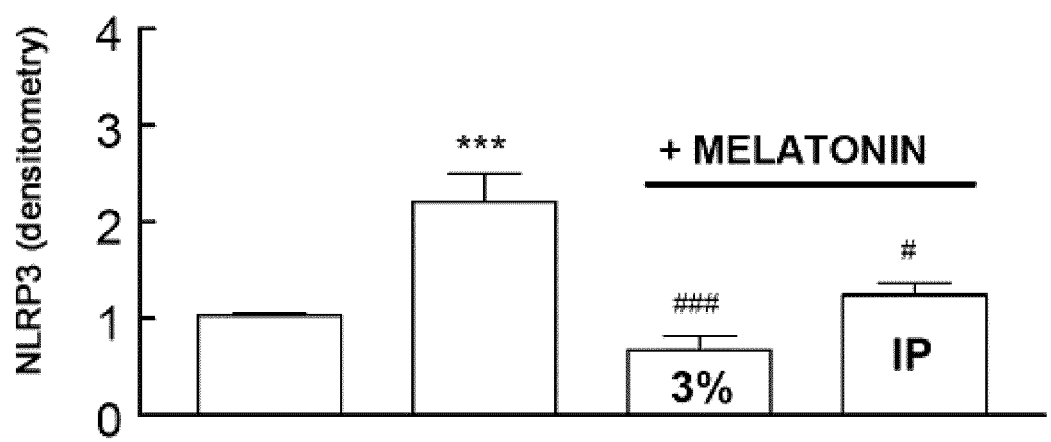
FIG. 15. Expression of NLRP3, ASC and caspase 1 by means of Western blot in a rat tongue homogenate from irradiated rats treated with melatonin gel by topical route in the oral cavity and with melatonin by intraperitoneal route. A, Western blot band densitometry corresponding to NLRP3; B, to ASC; C, to caspase 1 (casp. 1); D, Western blot image corresponding to NLRP3, ASC and caspase 1. Control rats (C), irradiated rats (IR), rats treated with 3% melatonin gel (+3% aMT), and treated with melatonin by i.p. route (+IP aMT). ***p<0.001 with respect to C; #p<0.05 with respect to IR.
Figure 15:
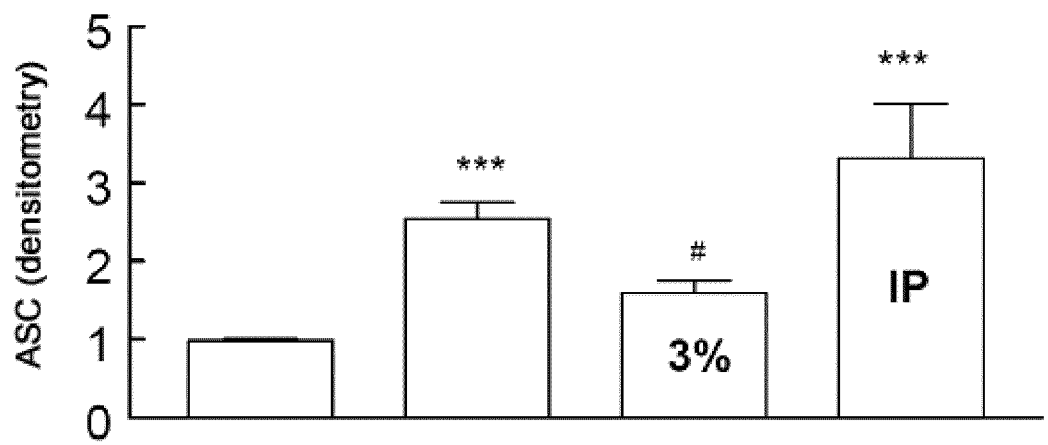
Figure 15:
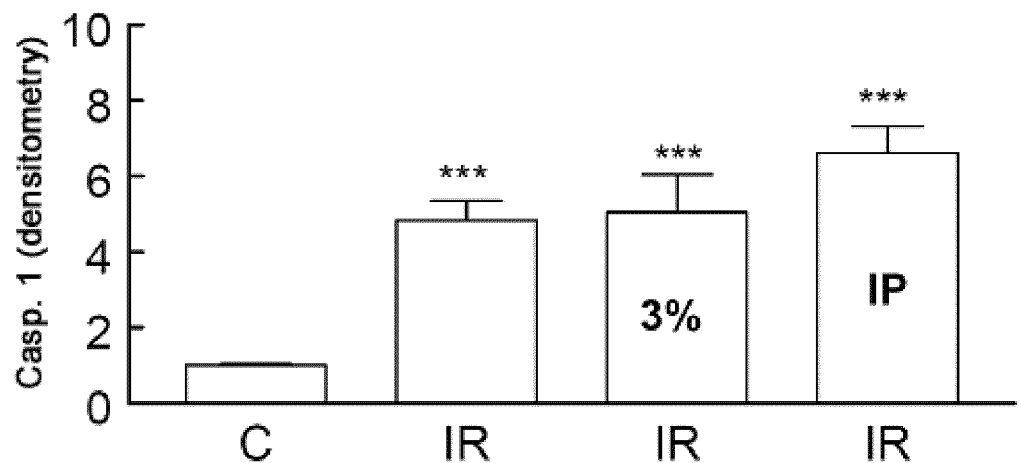
Figure 15:
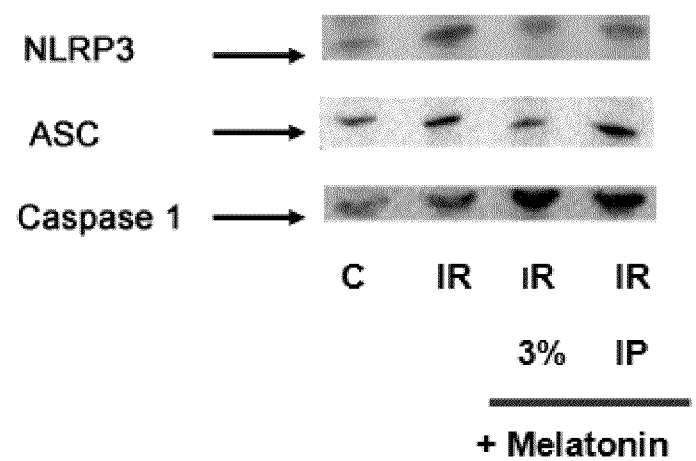
Figure 16:
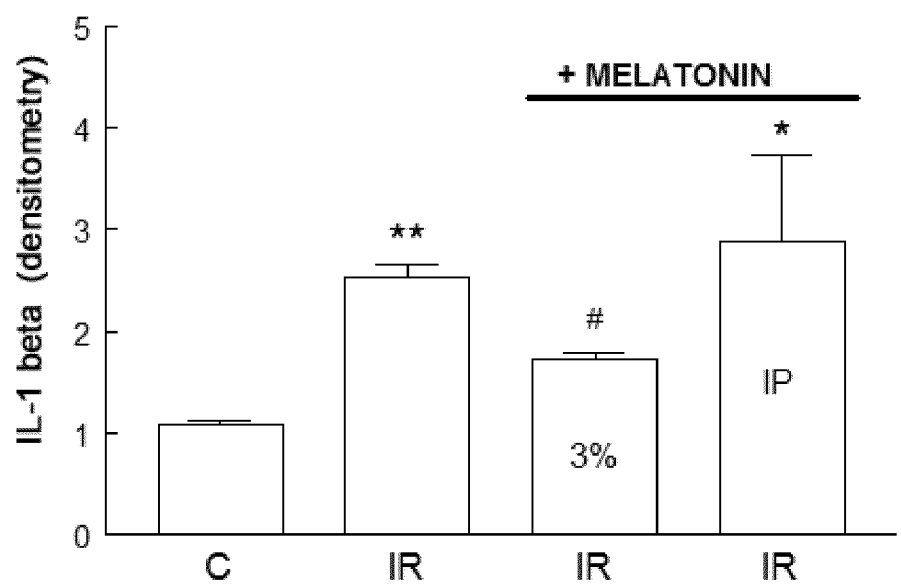
FIG. 16. Expression of IL-1 and TNF-α by means of Western blot in a rat tongue homogenate from irradiated rats treated with melatonin gel by topical route in the oral cavity and with melatonin by intraperitoneal route. A, Western blot band densitometry corresponding to IL-1; B, to TNF-α; C, Western blot image corresponding to IL-1 and TNF-α. Control rats (C), irradiated rats (IR), rats treated with 3% melatonin gel (+3% aMT), and treated with melatonin by i.p. route (+IP aMT). **p<0.01 and *p<0.05 with respect to C; ###p<0.01 and #p<0.05 with respect to IR.
Figure 16:
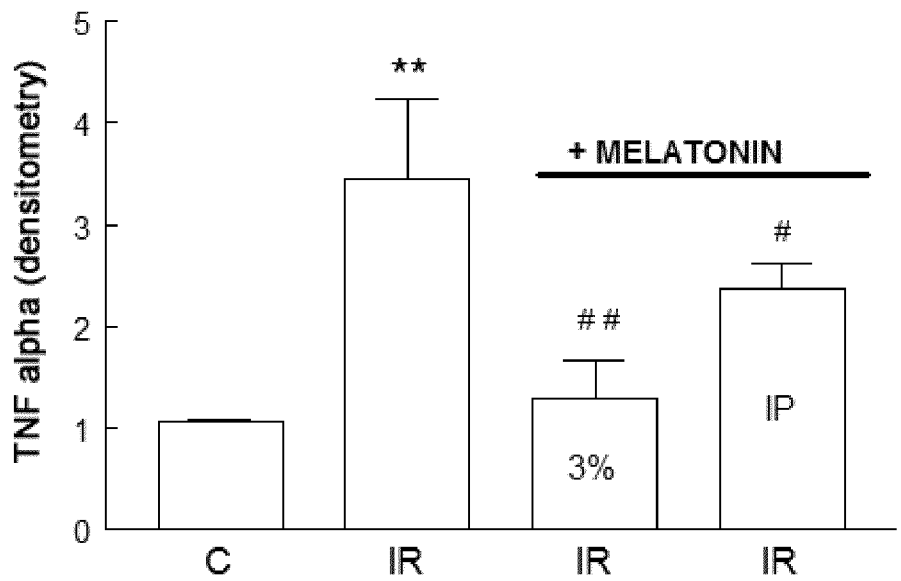
Figure 16:
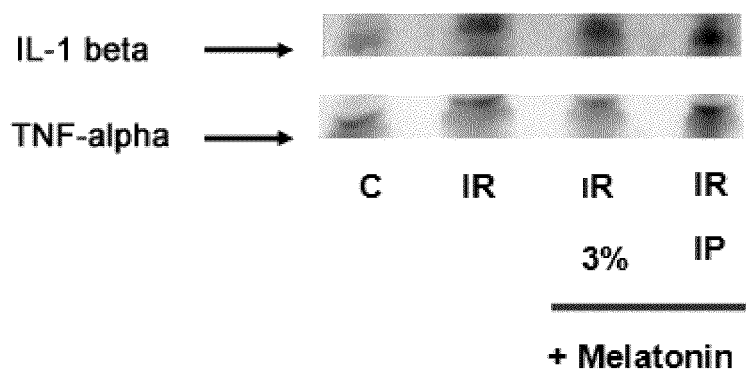

It is found that irradiation increases activation of NFkB, increasing levels both in the nucleus and in the cytosol (FIG. 14A and FIG. 14B), and the inflammasome pathway is activated, increasing NLRP3, ASC and caspase-1 (FIG. 15). As a result of activation of the NFkB pathway and inflammasome pathway, there is an increase in proinflammatory cytokines IL-1 and TNF-α (FIGS. 16A and 16B)

Figure 17:
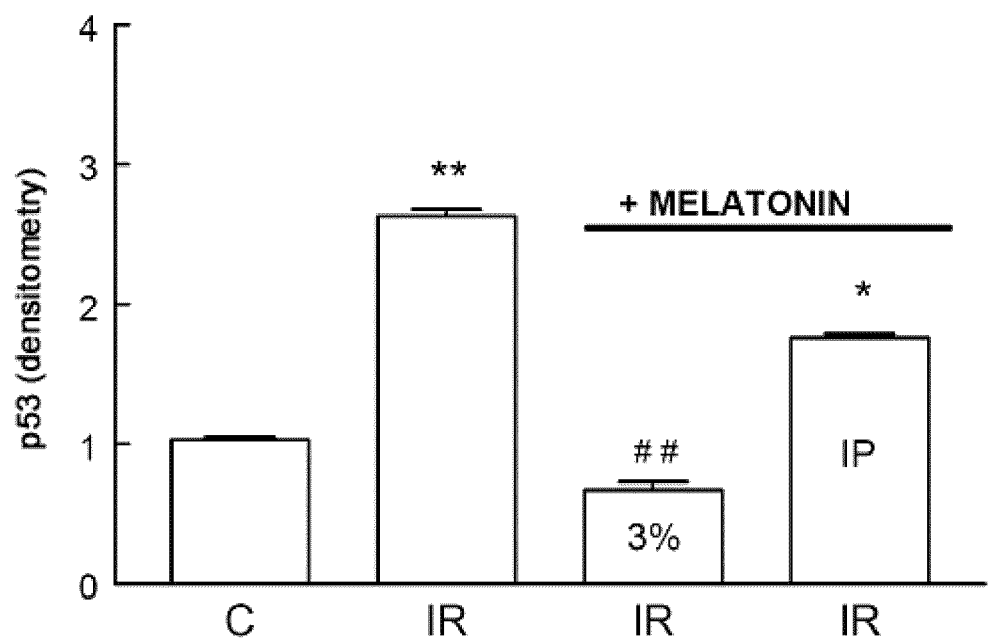
FIG. 17. Expression of P53, Bax and Bcl2 by means of Western blot in a rat tongue homogenate from irradiated rats treated with melatonin gel by topical route in the oral cavity and with melatonin by intraperitoneal route. A, Western blot band densitometry corresponding to P53; B, to Bax; C, to Bcl2; D, Bax/Bcl2 ratio; E, Western blot image corresponding to P53, Bax and Bcl2. Control rats (C), irradiated rats (IR), rats treated with 3% melatonin gel (+3% aMT), and treated with melatonin by i.p. route (+IP aMT). *p<0.001, p<0.01 and *p<0.05 with respect to C; ####p<0.001 and ###p<0.01 with respect to IR.
Figure 17:
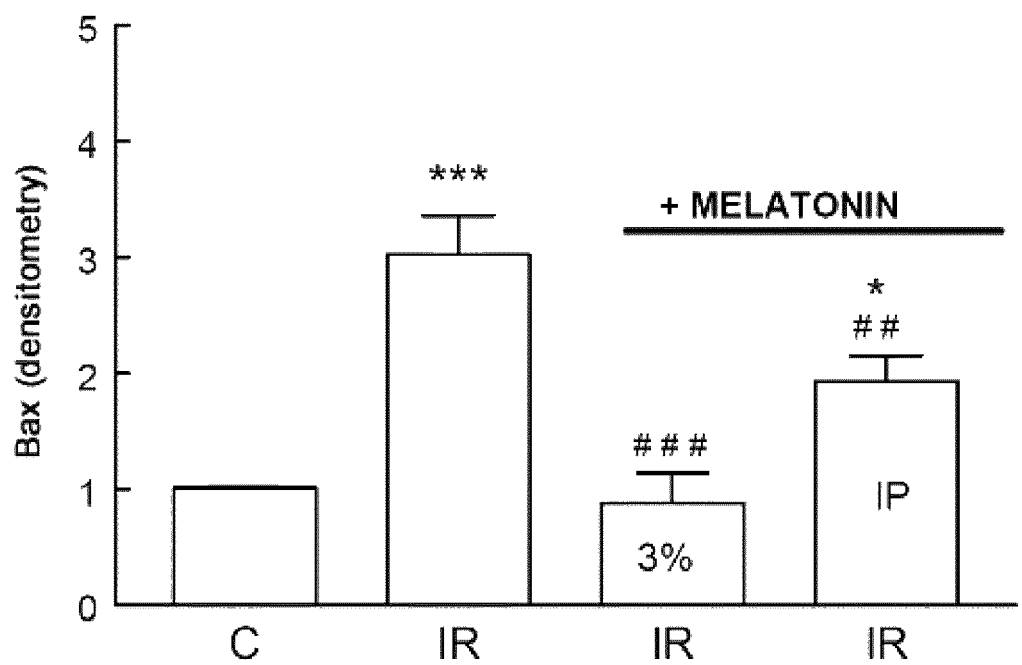
Figure 17:
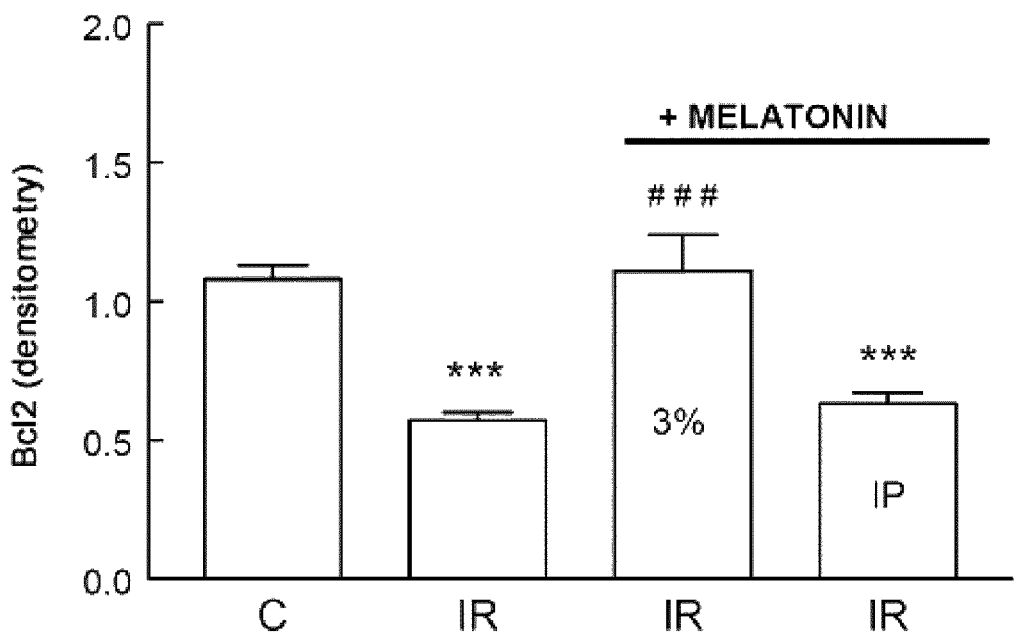
Figure 17:
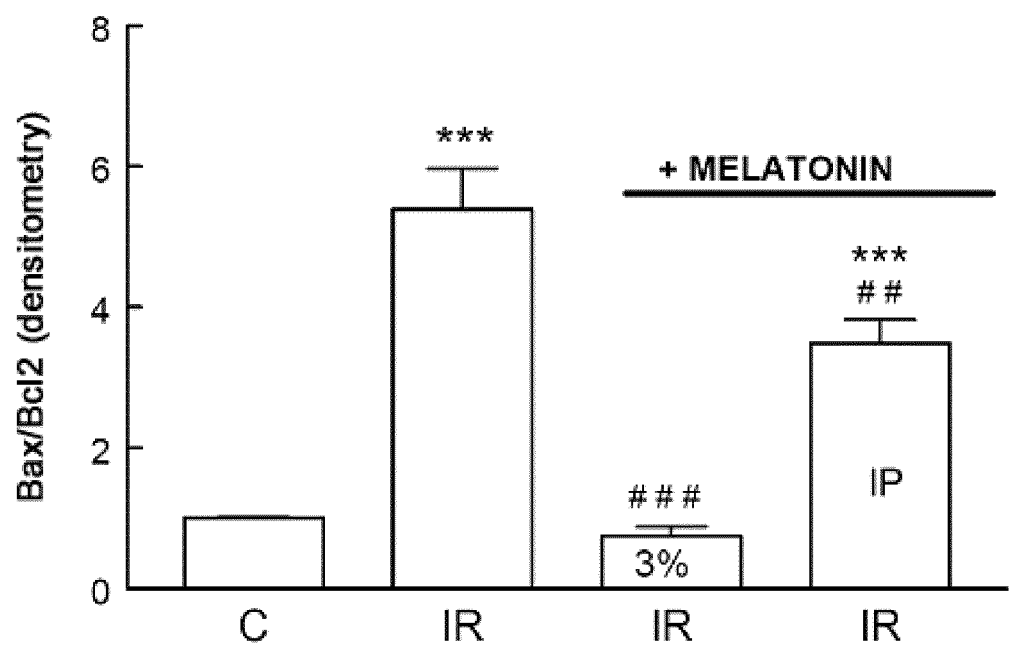
Figure 17:
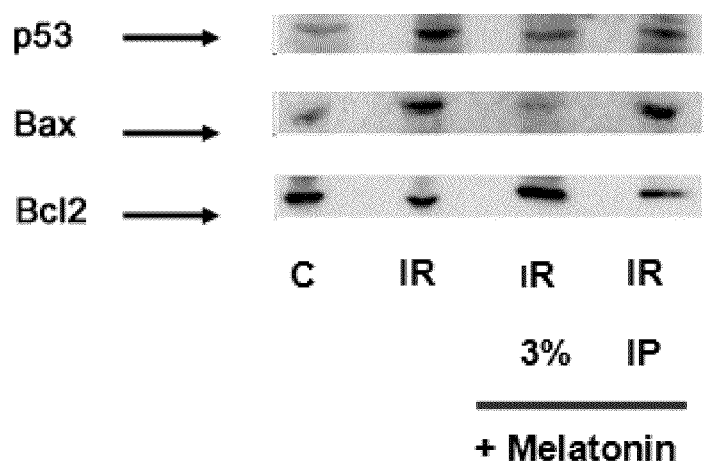

Mitochondrial damage also involves an increase in apoptosis, with an increase in proapoptotic proteins p53 (FIG. 17A) and Bax (FIG. 17B), as well as a decrease in antiapoptotic proteins such as Bcl2 (FIG. 17C). Therefore, there is an increase in the Bax/Bcl2 ratio and in p53 (FIG. 17D), indicating a significant increase in apoptosis.

This is the first time the direct relationship of mitochondrial damage, inflammasome activation and radiation-induced mucositis has been demonstrated.

In turn, administration of 3% melatonin gel neutralizes oxidative stress, increases activity and expression of antioxidant enzymes, increases mitochondrial function, reduces the production of free radicals decreasing activity of NFkB (FIGS. 14A and 14B) and of inflammasome (FIG. 15).

Therefore, 3% melatonin gel significantly inhibits apoptosis (FIG. 17D), decreasing apoptosis-inducing proteins such as p53 and Bax (FIGS. 17A and 17B), and increasing expression of antiapoptotic proteins such as Bcl2 (FIG. 17C).

Furthermore, 3% melatonin gel increases mitochondrial biogenesis, increasing PGC1α, which is inhibited with irradiation.

All this translates into an increase in cell survival. Furthermore, melatonin levels are restored with administration of the gel by topical route in the oral cavity, favoring local antioxidant action.

However, such levels are not restored in the tongue with the parenteral administration of melatonin. These results explain why topical administration is much more efficient than parenteral administration of melatonin.

Histology also shows macroscopic lesions. Hematoxylin-eosin staining was used to determine the presence of histological lesions in studied tissues. Masson Goldner's trichrome stain (TRI) allowed differentiating muscle tissue, which is stained red, from the connective tissue, which is stained green.

In the untreated control animal, the histological structure of the tongue has no alterations. The polystratified keratinized epithelium of the mucosa is maintained with the presence of filiform papillae in the dorsal zone and the absence thereof in the ventral zone. The lamina propria and the submucosa formed by a small layer of connective tissue and some vessels are under the mucosa. Then the layers of muscle are found, oriented in different directions and having a small amount of connective tissue between bundles. This scarcity of connective tissue is clearly shown with TRI staining, where the presence of green stain is minor between the tongue muscles.

In irradiated animals, there is an increase in connective tissue (fibrosis) between muscle fibers, separating them. There is also vascular congestion and a significant increase in the number of vessels (angiogenesis). Unlike what is observed in the control animal, in this case green-stained fibrosis is much more abundant. This is especially observed in the muscle layer where the fibers have been cut transversely.

In animals treated with melatonin a decrease in fibrosis and in angiogenesis between the muscle fibers of the tongue is observed in comparison with that observed in the tongue of irradiated animals. This decrease in fibrous connective tissue is best shown by means of the TRI technique because it is stained green, being perfectly distinguished from the muscle fibers that are stained red. Regarding the difference between both treatments, 3% melatonin gel worked better than the parenteral administration because fibrosis is much less.

All these effects of irradiation lead to mitochondrial damage that can be observed by means of electron microscopy. In irradiated animals, mitochondrial vacuolization as well as broken mitochondria with a loss of the content thereof, causing an increase in free radicals and in the inflammatory response, can be observed.

In animals treated with the gel, broken mitochondria are not observed and the vacuoles disappear. However, broken mitochondria are observed in rats treated with melatonin by parenteral route, as in untreated animals.

Therefore, it has been demonstrated for the first time that melatonin allows protecting the gastrointestinal mucosa subjected to radiotherapy, preventing lesions caused by said radiations, such as mucositis, and curing said lesions, administration by topical route being more efficient than parenteral administration. The importance of these actions of melatonin is based on a reduction in mitochondrial damage, which translates into complete prevention of mucositis, no lesion whatsoever being observed in the treated rats at the macroscopic level or microscopic level.

D—Example 2

Results Obtained in Humans

Patients treated with 3% melatonin gel withstand radiotherapy much better, not requiring treatment with opioids. None of these patients needed a nasogastric tube, none was hospitalized and none had to interrupt treatment. Patients not treated with melatonin all needed major opioids and they all developed maximum grade of radiation dermatitis. Some had to be hospitalized, interrupting treatment.

E—Conclusion of the Examples of the Invention

The pharmaceutical composition comprising 1% melatonin does not reverse mucositis caused by radiotherapy. However, the pharmaceutical composition comprising 3% melatonin completely reverses mucositis caused by radiotherapy, as occurs with the composition comprising 5% melatonin. These results demonstrate the usefulness of a composition comprising between 3% and 5% melatonin in the treatment of the side effects of mucositis caused by radiotherapy.

The results herein shown demonstrate that there is mitochondrial damage in mucositis, and therefore success of this treatment is based on the oral application of a melatonin gel which impregnates the mucosae and reverses mitochondrial damage. Any other type of melatonin application has no clear effect on mucositis, probably due to the fact that melatonin is quickly absorbed, has a very short half-life (30 minutes), and does not reach sufficient therapeutic levels in the mucosae both in the oral cavity and in the gastrointestinal tract. However, the composition of the invention comprising Pluronic F-127 and melatonin gel at the 3% concentration or higher impregnates the mucosae, reaching effective local concentrations, allowing melatonin to enter the mitochondrion and exert its effects on the entire gastrointestinal tract.

Therefore, these pharmaceutical formulations for topical application in the buccal cavity containing melatonin at doses suitable for protecting the skin and mucosae against terrible damage caused by radiations during the radiotherapy periods have a huge clinical interest. It has been found that parenteral administration of melatonin provides no benefit whatsoever with respect to topical administration in the oral cavity for treating and/or preventing mucositis, with the added value that chronic parenteral administration is traumatic for these patients, topical administration of the gel being much more comfortable.

Mitochondria play an important role in controlling cell survival, and it has been demonstrated herein for the first time that mitochondrial dysfunction participates to a large extent in the physiopathology of mucositis (see results). Mitochondrial dysfunction correlates with a worsening of mucositis. For the first time, it has been found that in the tongue mitochondria from rats with mucositis, in addition to bioenergetic failure, there is an increase in glutathione peroxidase (GPx), a reduction in glutathione reductase (GRd), and an increase in the oxidized glutathione (GSSG)/reduced glutathione (GSH) (GSSG/GSH) ratio. The latter is an accurate marker of intracellular and intramitochondrial oxidative stress.

The present invention demonstrates that melatonin at the concentration contained in the composition of the invention completely reduces mitochondrial oxidative stress in mucositis increasing activity of mitochondrial antioxidant enzymes, mainly GRd. In parallel, there is an increase in activity and expression of respiratory chain complexes, which are inhibited in mucositis. The composition of the invention has antioxidant and anti-inflammatory effects that compositions with a lower concentration do not have. The topical and oral application of between 3 and 5% melatonin (3 and 5 grams of melatonin in 100 ml of the final composition) prevents impairment of cell function of the mucosae damaged by ionizing radiations.

Furthermore, topical application in the buccal cavity by means of melatonin gel is more efficient in mucositis than parenteral administration, which may be due to the fact that application in the oral cavity in the suitable formulation maintains higher melatonin levels for a longer period of time in the oral cavity (and by extension, in the gastrointestinal tract), which facilitates the local antioxidant and anti-inflammatory action, and fundamentally action inside the mitochondrion, preventing tissue damage, and therefore the onset of mucositis. Therefore, topical application of between 3% and 5% melatonin in the oral cavity provides a potent defense system in these pathologies. It has been demonstrated that the composition of the invention allows protecting the gastrointestinal mucosa subjected to radiotherapy, preventing lesions caused by said radiation, such as mucositis, and curing said lesions. The obtained results can be extrapolated to chemotherapy.

The invention claimed is:

1. A method for treating and/or preventing mucositis, the method comprising topically administering a gel composition comprising: a compound of general formula (I):

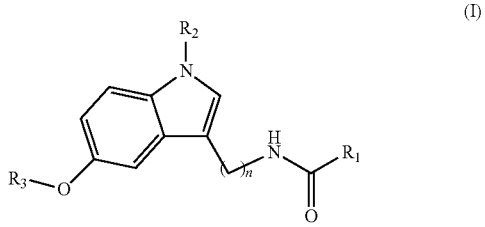

where:
"n" is an integer between 1 and 4;
$R_1$ and $R_3$ are independently selected from the group consisting of linear ($C_1$-$C_4$) alkyl groups and branched ($C_1$-$C_4$) alkyl groups; and
$R_2$ is hydrogen, a linear or branched ($C_1$-$C_4$) alkyl group, a —C(=O)O—Ra group or a —C(=O)—N(H)—Ra group; where Ra is a linear or branched ($C_1$-$C_4$) alkyl group,
or the salts, prodrug and solvate thereof,
where said compound is at a concentration of 2.5 to 5% w/v.

2. The method according to claim 1, wherein $R_1$ and $R_3$ are independently selected from the group consisting of ($C_1$-$C_2$) alkyl groups.

3. The method according to claim 2, wherein $R_1$ and $R_3$ are a methyl group.

4. The method according to claim 1, wherein n is 1.

5. The method according to claim 1, wherein $R_2$ is hydrogen.

6. The method according to claim 1, wherein the compound is melatonin.

7. The method according to claim 1, wherein the concentration of the compound is 3% w/v.

8. The method according to claim 1, wherein the mucositis is caused by radiotherapy and/or chemotherapy.

9. The method according to claim 1, wherein the mucositis is oral, pharyngeal, esophageal, stomach or intestinal mucositis.

10. The method according to claim 9, wherein the mucositis is oral mucositis.

11. The method according to claim 1, wherein the mucositis is in humans.

12. The method according to claim 1, wherein the composition further comprises at least one pharmaceutically acceptable excipient or adjuvant.

13. The method according to claim 1, wherein the composition further comprises a gelling agent.

14. The method according to claim 13, wherein the gelling agent is selected from the list comprising polyethylene and polypropylene copolymer, cellulose and guar gum.

15. The method according to claim 1, wherein the composition further comprises at least one preservative.

16. The method according to claim 1, wherein the composition further comprises an antioxidant.

17. The method according to claim 1, wherein the composition further comprises a pharmaceutically acceptable carrier.

* * * * *